United States Patent [19]
Green et al.

[11] Patent Number: 5,395,381
[45] Date of Patent: Mar. 7, 1995

[54] APPARATUS AND METHOD FOR APPLYING LATCHLESS SURGICAL CLIPS

[75] Inventors: David T. Green, Westport; Daniel Shichman, Trumbull, both of Conn.; Boris Zvenyatsky, Bronx, N.Y.; Richard A. McGarry, Norwalk, Conn.

[73] Assignee: United States Surgical Corporation, Norwalk, Conn.

[21] Appl. No.: 81,630

[22] Filed: Jun. 23, 1993

Related U.S. Application Data

[63] Continuation-in-part of Ser. No. 626,841, Dec. 13, 1990.

[51] Int. Cl.⁶ .............................................. A61B 17/04
[52] U.S. Cl. ....................................... 606/143; 227/19
[58] Field of Search ............... 606/142, 143, 219, 151, 606/158; 227/175–180, 19

[56] References Cited

U.S. PATENT DOCUMENTS

| | | | |
|---|---|---|---|
| 3,631,707 | 1/1972 | Miller | 606/142 |
| 3,757,629 | 9/1973 | Schneider . | |
| 3,777,538 | 12/1973 | Weatherly et al. | 606/142 |
| 3,882,854 | 5/1975 | Hulka et al. | 128/6 |
| 3,955,581 | 5/1976 | Spasiano et al. | 227/19 |
| 4,027,510 | 6/1977 | Hiltebrandt | 128/6 |
| 4,038,987 | 8/1977 | Komiya | 606/142 |
| 4,064,881 | 12/1977 | Meredith | 606/142 |
| 4,152,920 | 5/1979 | Green . | |
| 4,169,476 | 10/1979 | Hiltebrandt | 606/142 |
| 4,196,836 | 4/1980 | Becht | 227/19 |
| 4,228,895 | 10/1980 | Larkin | 206/339 |
| 4,246,903 | 1/1981 | Larkin | 606/142 |
| 4,317,451 | 3/1982 | Cerwin et al. . | |
| 4,396,139 | 8/1983 | Hall et al. | 227/19 |
| 4,418,694 | 12/1983 | Beroff et al. | 606/157 |
| 4,476,865 | 10/1984 | Failla et al. | 606/157 |
| 4,492,232 | 1/1985 | Green | 606/143 |
| 4,509,518 | 4/1985 | McGarry et al. | 606/143 |
| 4,512,345 | 4/1985 | Green | 606/143 |
| 4,527,562 | 7/1985 | Mericle | 606/157 |
| 4,550,715 | 11/1985 | Santangelo et al. | 128/4 |
| 4,557,263 | 12/1985 | Green . | |
| 4,562,839 | 1/1986 | Blake, III et al. | 606/142 |
| 4,590,937 | 5/1986 | Deniega . | |
| 4,616,650 | 10/1986 | Green et al. | 606/143 |
| 4,620,541 | 11/1986 | Gertzman et al. | 606/157 |
| 4,624,254 | 11/1986 | McGarry et al. | 606/143 |
| 4,638,804 | 1/1987 | Jewusiak | 606/142 |
| 4,646,741 | 3/1987 | Smith | 606/219 |
| 4,662,373 | 5/1987 | Montgomery et al. | 606/143 |
| 4,712,549 | 12/1987 | Peters et al. | 606/143 |
| 4,741,337 | 5/1988 | Smith et al. | 606/219 |
| 4,796,627 | 1/1989 | Tucker | 606/143 |
| 4,821,721 | 4/1989 | Chin et al. . | |
| 4,822,348 | 4/1989 | Casey . | |
| 4,858,608 | 8/1989 | McQuilkin | 606/142 |
| 4,919,152 | 4/1990 | Ger | 128/898 |
| 4,944,443 | 7/1990 | Oddsen et al. | 227/19 |
| 4,950,258 | 8/1990 | Kawai et al. . | |
| 4,983,176 | 1/1991 | Cushman et al. . | |
| 5,084,057 | 1/1992 | Green et al. | 606/142 |
| 5,100,420 | 3/1992 | Green et al. | 606/143 |
| 5,156,609 | 10/1992 | Nakao et al. | 606/143 |

FOREIGN PATENT DOCUMENTS

| | | |
|---|---|---|
| 2330182 | 1/1975 | Germany . |
| 3802651 | 8/1989 | Germany . |
| 9003763 | 4/1990 | WIPO . |

Primary Examiner—Stephen C. Pellegrino
Assistant Examiner—Gary Jackson

[57] ABSTRACT

A disposable apparatus is disclosed for applying latchless surgical clips to body tissue in endoscopic surgical procedures. The latchless clips are resiliently biased to a closed configuration. The apparatus includes a frame which is adapted to be gripped by hand, and an endoscopic section connected to the handle and capable of storing surgical clips in preparation for clipping arteries or other body tissue. The apparatus includes means for advancing each clip sequentially, temporarily opening the clip and advancing the clip further to a pair of distal jaws where the clip is positioned around the body tissue and closes around the tissue. Also included are means for closing the jaws about the clip. When the jaws are closed, the clip advancing means is simultaneously positioned to advance the next clip. The present apparatus also makes it possible to partially close a clip without interfering with the sequential movement of the clip advancing mechanism.

24 Claims, 14 Drawing Sheets

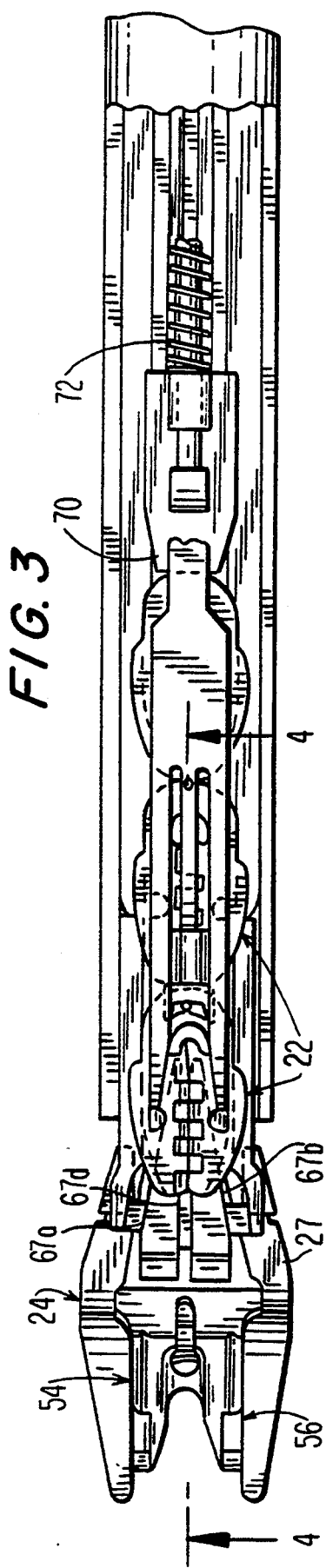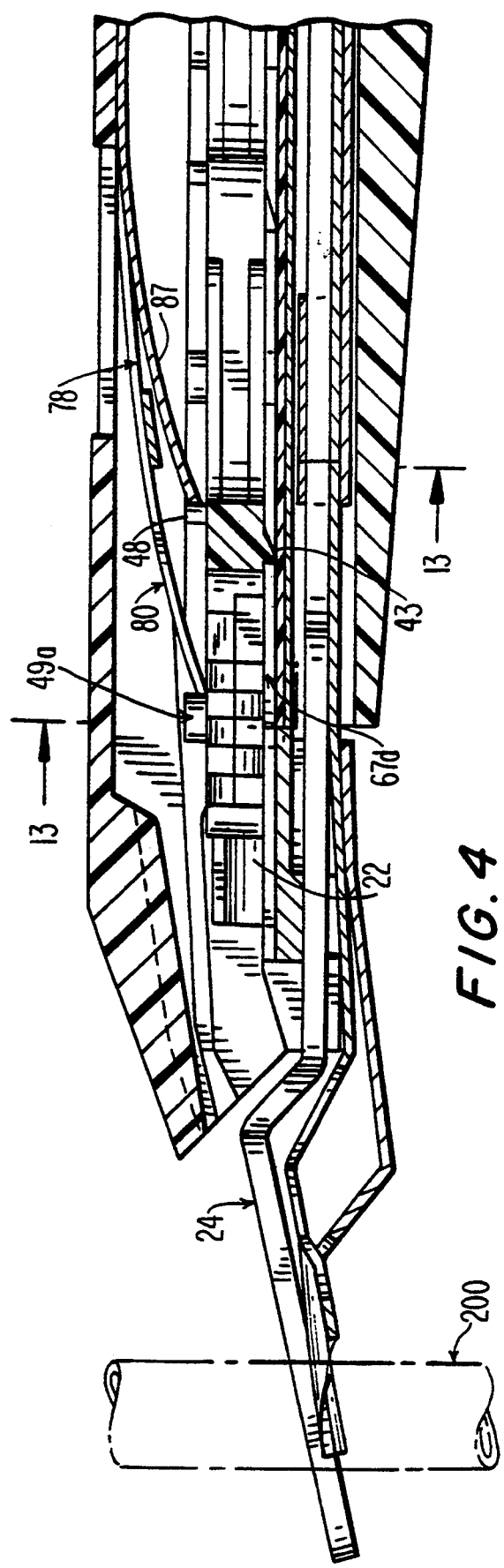

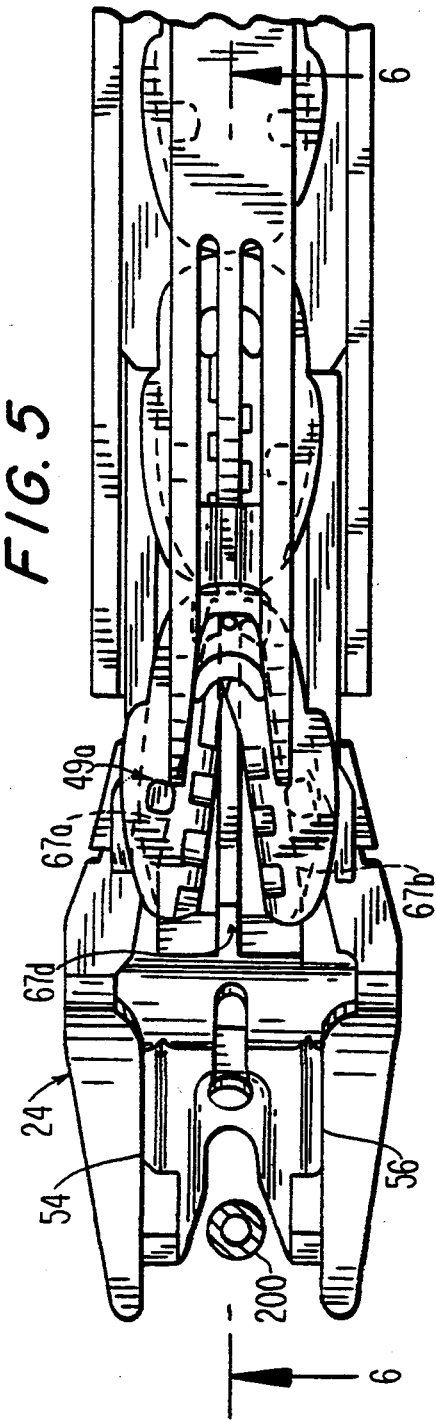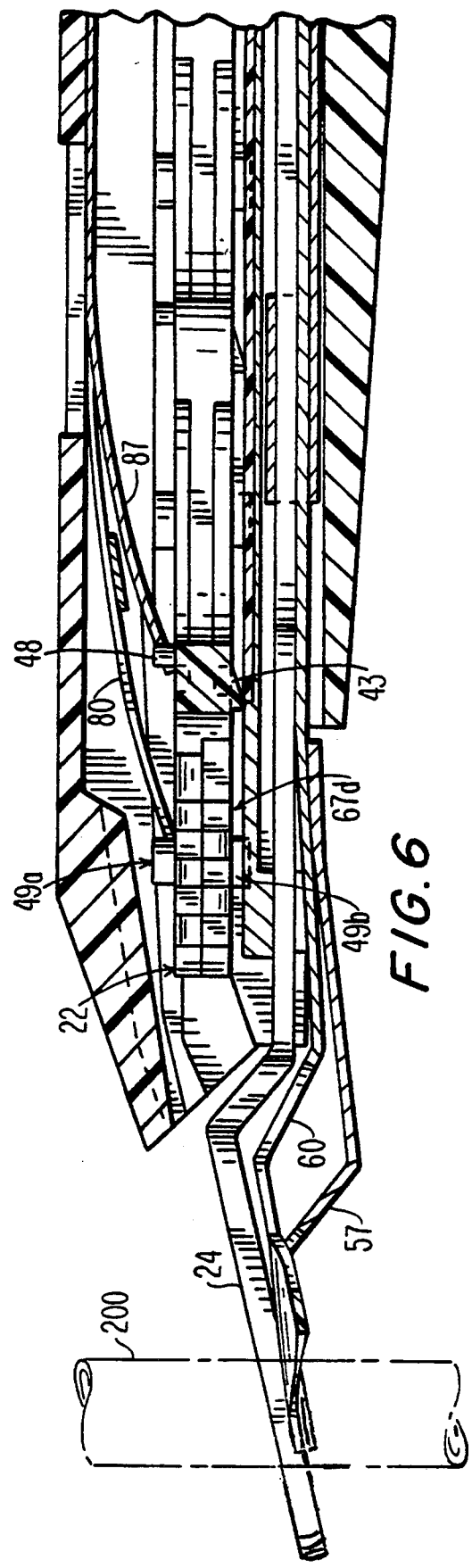

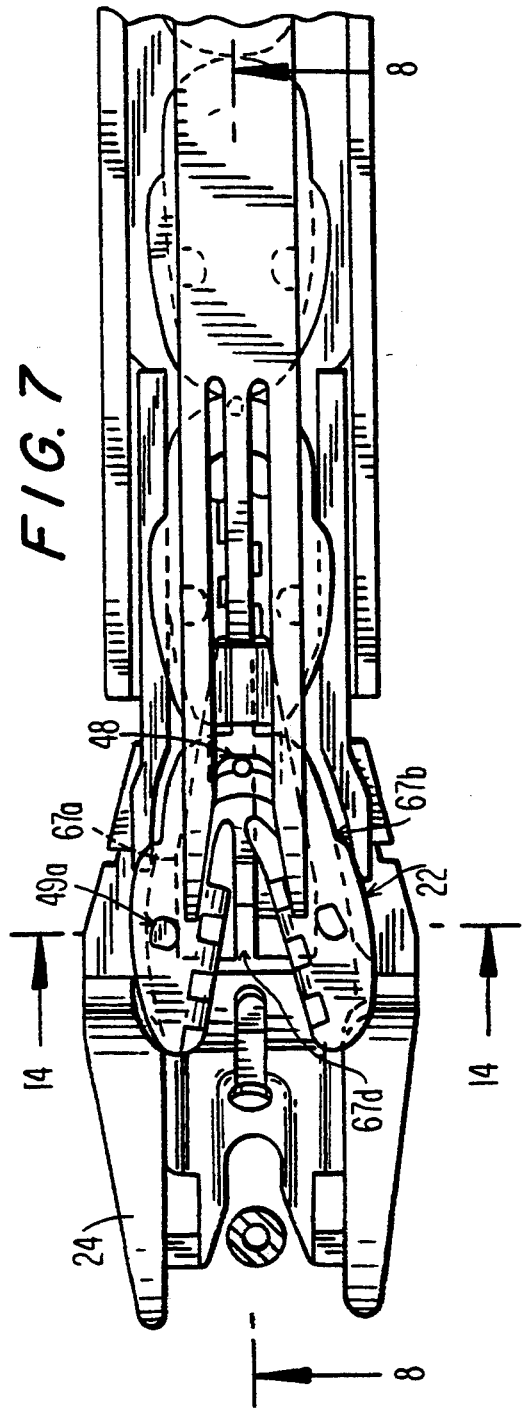
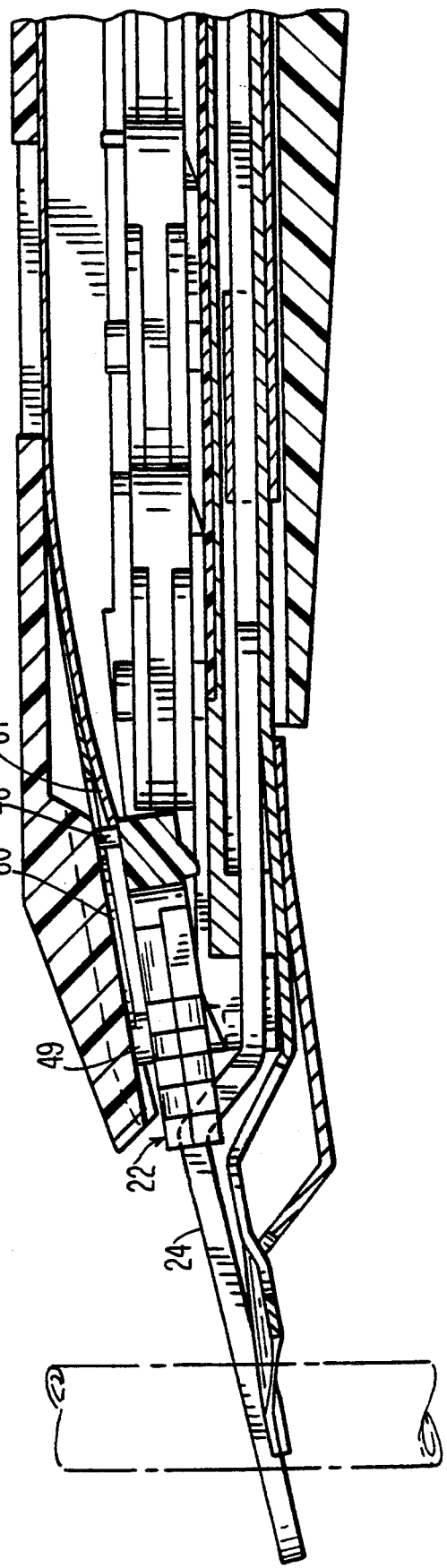

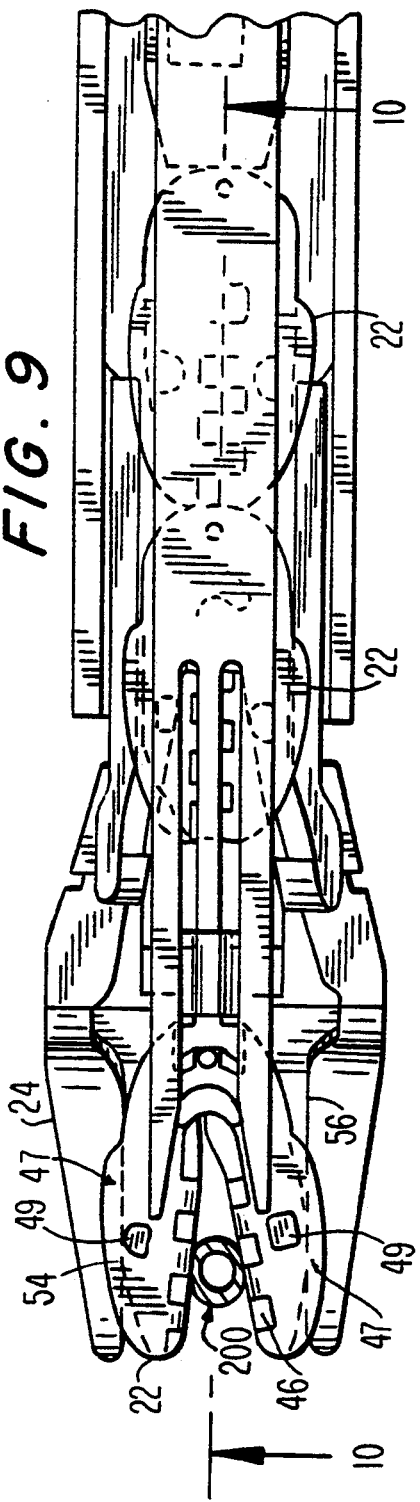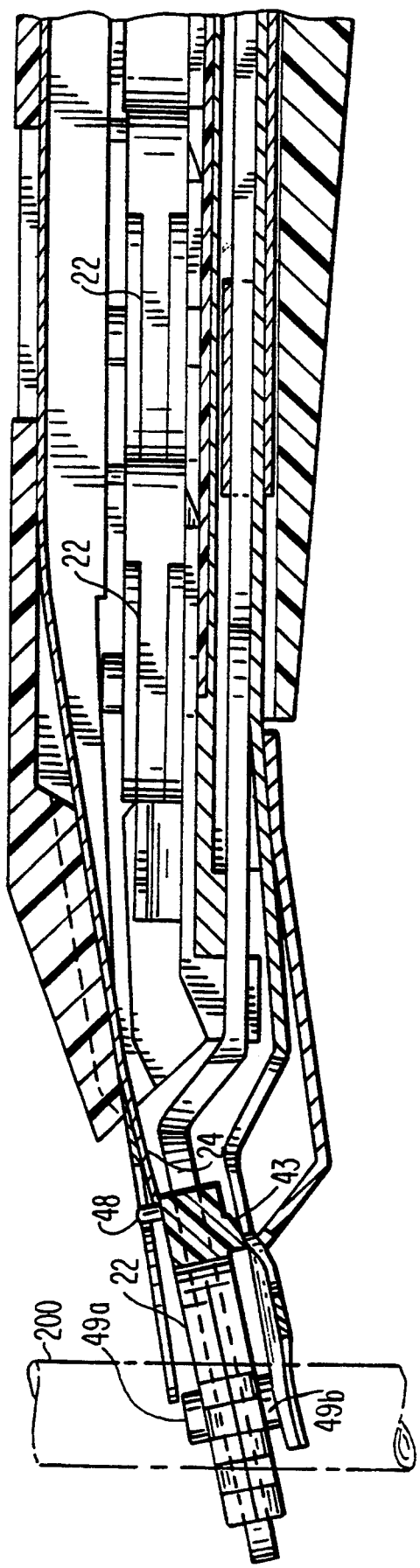

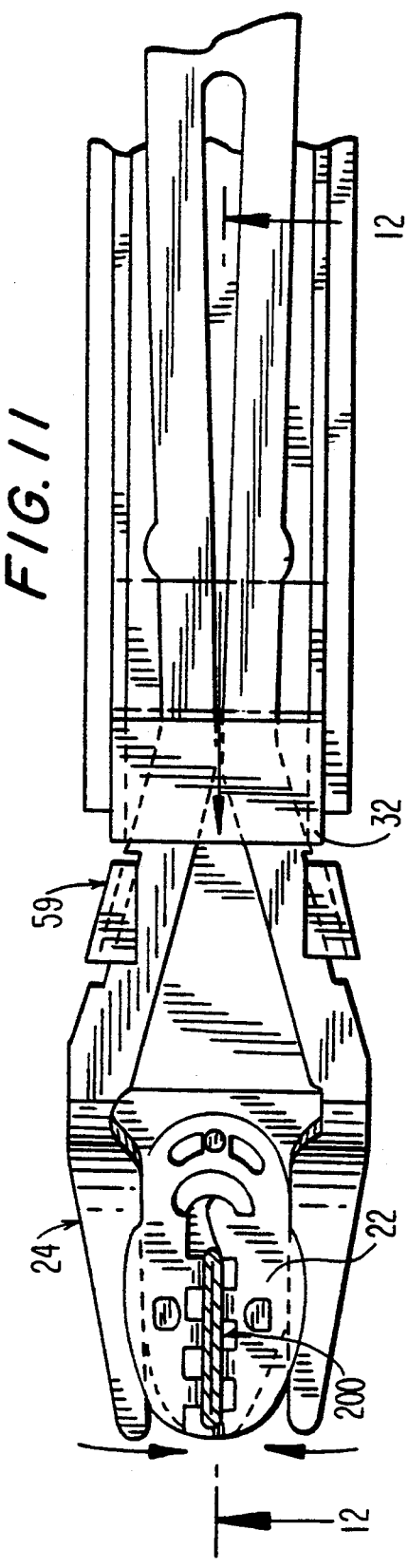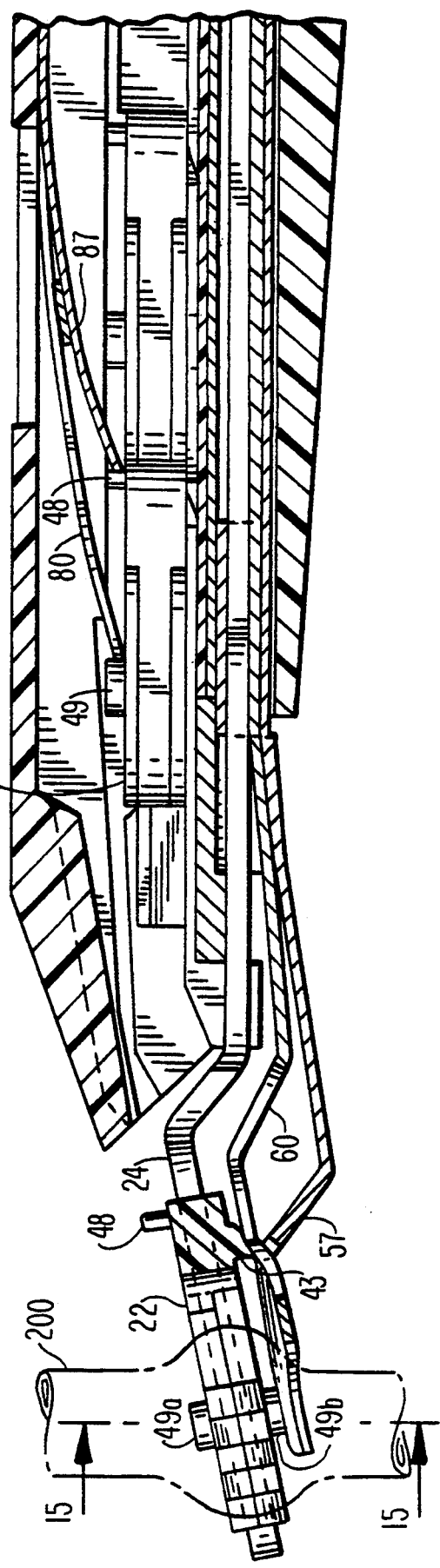

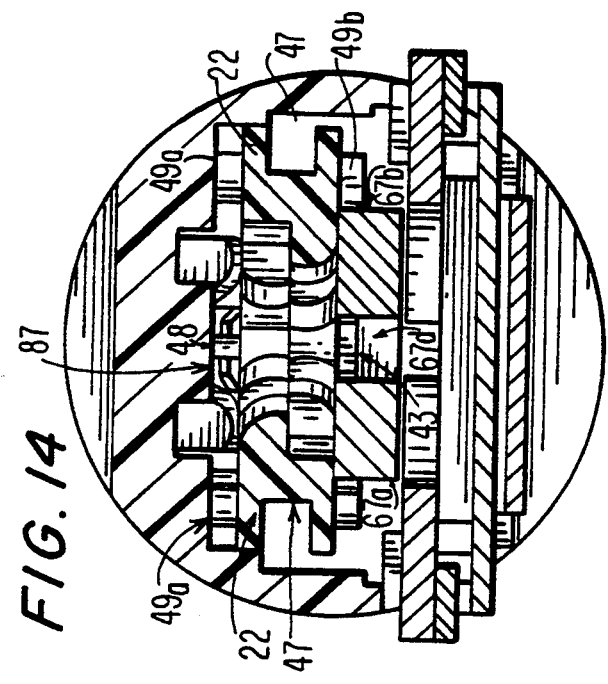
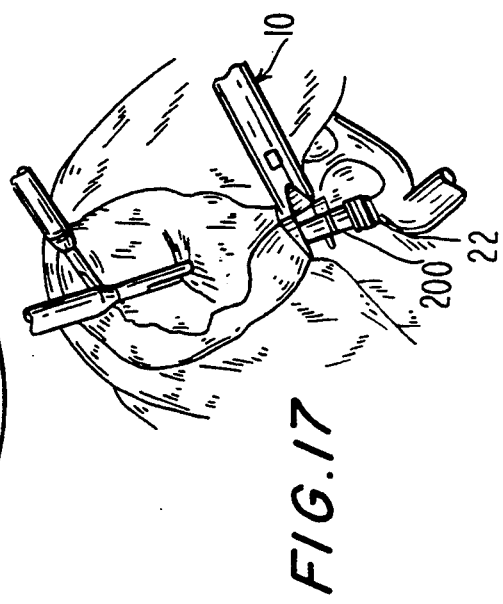
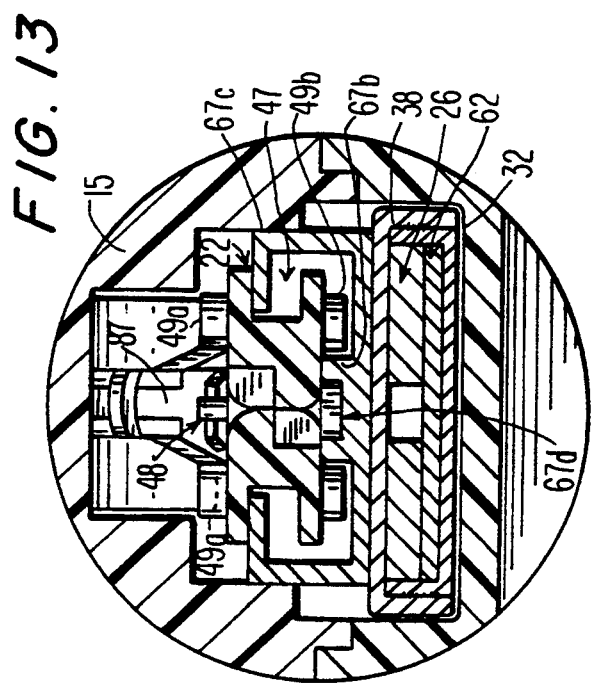
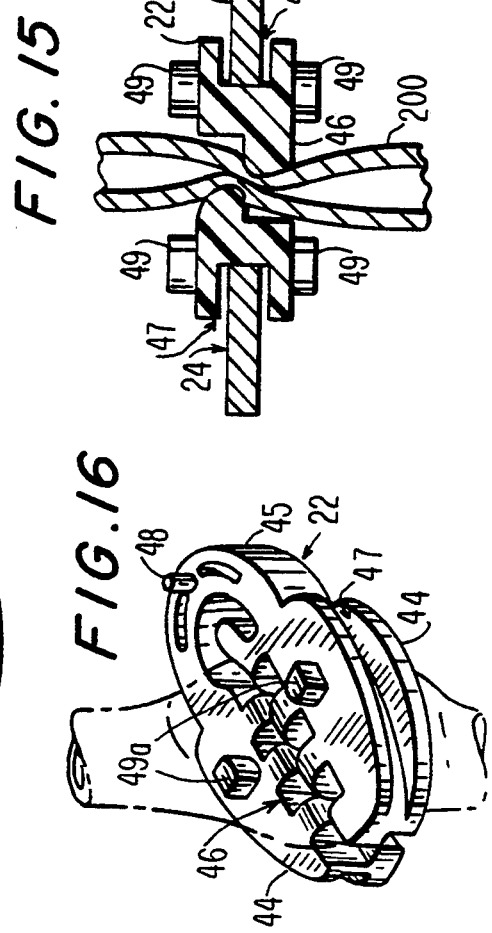

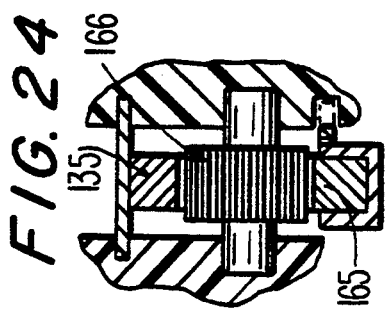
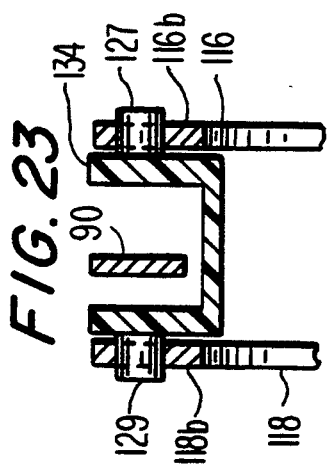
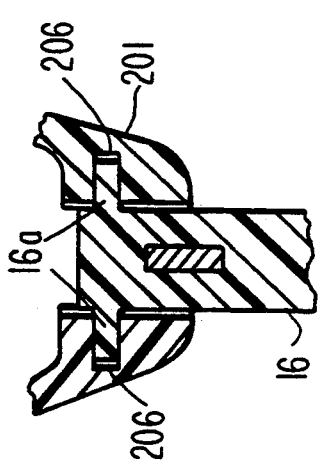
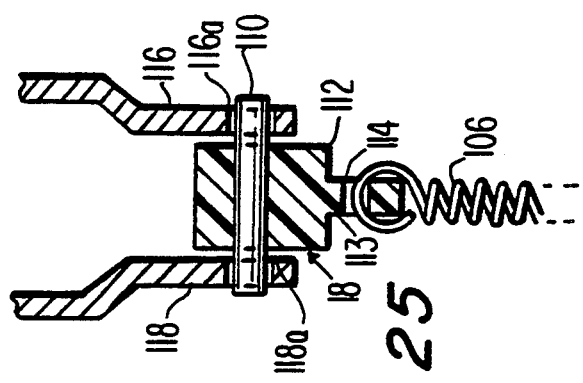

APPARATUS AND METHOD FOR APPLYING LATCHLESS SURGICAL CLIPS

CROSS REFERENCE TO RELATED APPLICATIONS

This is a continuation-in-part of U.S. application Ser. No. 626,841, filed Dec. 13, 1990.

BACKGROUND OF THE INVENTION

1. Field of the Invention

This invention relates to an apparatus and method for applying surgical clips, especially hemostatic clips, to body tissue such as blood vessels. More particularly, this invention relates to a surgical clip applier which can be used in laparoscopic or endoscopic procedures for closing ducts, arteries and the like, and to a method for using same.

2. Background of the Art

In surgical operations it is often necessary to apply hemostatic clips to blood vessels, and apparatus for applying clips are known in the art. See, for example, U.S. Pat. No. 4,616,650 and 4,624,254, both of which are hereby incorporated by reference in their entirety, which disclose a surgical clip applying apparatus having ring-like handles. The handles are squeezed to force jaws to move distally relative to the apparatus where they are forced together by a pair of inclined surfaces. A surgical clip between the jaws is thereby squeezed closed.

While the instruments described in the above-referenced patents have provided beneficial features to surgeons in conventional surgical procedures, they are not useful in endoscopic or laparoscopic operations. In laparoscopic procedures surgery is performed in the interior of the abdomen through a small incision; in endoscopic procedures surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insuffiated. Moreover, laparoscopic and endoscopic procedures often require the surgeon to act on organs, tissues, and vessels far removed from the incision, thereby requiring that any instruments to be used in such procedures be both long and narrow. In either laparoscopic or endoscopic surgery, the functional portion of the instrumentation is controlled from outside the body. Mechanical actuation of such instruments is for the most part constrained to movement of the various components along a longitudinal axis, even if lateral movement is employed at the operating site. The initial opening in the body tissue to allow passage of the endoscopic tube to the interior of the body can be a natural passageway of the body (e.g. bronchial tubes), or it can be created by a tissue piercing instrument such as a trocar. Because the endoscopic or laparoscopic tubes, instrumentation, and any required puncture are relatively narrow, endoscopic or laparoscopic surgery is less invasive and causes much less trauma to the patient as compared with procedures in which the surgeon is required to cut open large areas of body tissue.

An endoscopic apparatus for applying surgical clips is described in U.S. Pat. Nos. 5,084,057 and 5,100,420, both of which are incorporated herein by reference in their entirety. The apparatus described in these patents apply generally U-shaped or V-shaped clips fabricated from a metal such as titanium or stainless steel. The clips are positioned between the jaws of the instrument which are then closed to squeeze the clip legs together.

As an alternative to metal, polymers are also used to fabricate surgical clips. The polymers can be bioabsorbable or non-bioabsorbable. Surgical clips fabricated from polymers are described in U.S. Pat. Nos. 4,418,694; 4,476,865; 4,492,232; 4,512,345; 4,527,562; 4,557,263; 4,590,937; 4,620,541; 4,638,804; 4,646,741; and 4,741,337. Bioabsorbable polymers include, for example, homopolymers and copolymers of lactide, glycolide, caprolactone and p-dioxanone. These polymers have the advantage of decomposing in the body after a period of time. A separate operation to remove them is unnecessary. Therefore, they can be used in situations where the clip is not intended to be permanently placed in the body. Non-bioabsorbable polymers which are known to be useful for the manufacture of surgical clips include polyesters, polyamides, polycarbonates, polyvinyl chlorides, polysulfones, and polypropylenes.

Up to the present, polymeric clips have been latched, i.e. the opposing "arm" or "leg" members which clamp the body tissue lock together by means of some type of latch mechanism. More recently, another type of polymeric surgical clip has been developed which is latchless. A latchless polymeric surgical clip is disclosed in commonly assigned U.S. patent application Ser. No. 07/626,841, filed Dec. 13, 1990, herein incorporated by reference in its entirety. Up to the present, it has been desirable to develop an apparatus for applying latchless clips. The present invention provides an apparatus and method for applying such latchless clips.

SUMMARY OF THE INVENTION

An apparatus is disclosed for applying latchless surgical clips to body tissue. The latchless clips each possess a pair of legs movable between a closed position wherein the legs are in relatively close proximity to each other and an open position wherein the legs are relatively spaced apart from each other. The legs are resiliently biased to the closed position. The apparatus comprises frame means, and endoscopic means of generally elongated configuration connected to the frame means and extending distally therefrom. The endoscopic means includes: means for storing a plurality of latchless surgical clips, means for opening the clips, means for selectively advancing the clips to the distal portion of the endoscopic means for positioning adjacent the body tissue to be clipped where the clips are permitted to at least partially close; and means for facilitating substantially complete closure of each clip at least sufficient to grip the body tissue. The apparatus may be completely disposable and the endoscopic means may be replaceable so as to permit additional clips to be applied with a single apparatus during a single surgical procedure.

In one embodiment, a disposable apparatus is disclosed for applying surgical clips to body tissue which comprises a frame configured and dimensioned for manual gripping, an elongated endoscopic section connected at the proximal end thereof to the frame and extending distally therefrom, the endoscopic section including means for storing a plurality of latchless surgical clips in generally aligned relation facing the distal portion thereof, jaw means positioned at the distal end thereof and adapted for sequential reception of the latchless clips, means for sequentially advancing and opening the latchless clips distally so as to be positioned between the jaw means for positioning adjacent the body tissue to be clipped, and means for sequentially at least partially closing the jaw means about each clip after the clip is advanced therebetween while simultaneously repositioning the clip advancing means for distal advancement of the next clip.

Preferably, an instrument body is provided and an actuating handle mounted to the instrument body, with first transmission means for linearly transferring motion from the actuating handle to the clip advancing means and means to close the jaw means. Second transmission means is provided for linearly transferring motion from the actuating handle to the jaw closing means, and means is provided for locking the handle such that after actuating the handle to close the jaws the handle cannot be actuated unless the locking means is released. The endoscopic section is rotatable independent of the handle, with means being provided to selectively lock the endoscopic section at a predetermined angular orientation relative to the handle. Means is provided to release the lock means of the endoscopic section so as to permit rotation thereof relative to the handle. Handle locking means comprises a first resilient catch movable in response to actuation of the handle from an unlocked position to a locked position wherein the first transmission means is advanced and locked. Release means is adapted to release the first resilient catch, the first resilient catch being returnable to the unlocked position in response to actuation of the release means. A second resilient catch is movable in response to actuation of the handle from an unlocked position to a locked position wherein it engages and locks the second transmission means. The second resilient catch is resiliently returnable to the unlocked position in response to the release of the resilient catch. The first transmission means comprises means responsive to actuation of the release means to release the second transmission means.

The jaw means preferably comprises a pair of jaws positioned in spaced relation and configured and dimensioned for reception of a latchless surgical clip therebetween. The jaws are resiliently movable toward and away from each other in response to distal movement of a camming means from a proximal position to a distal position. The camming means comprises a channel member slidably mounted within the endoscopic section and longitudinally movable in response to actuation of the handle, the channel member having at least two distal camming surfaces for biasing the jaws into the closed position. Means for storing latchless surgical clips comprises a track for holding a longitudinal array of latchless surgical clips, and resilient means located proximal to the array of latchless surgical clips for biasing the clips toward the distal direction. A clip track is positioned between the jaw means and The clip follower. Means for advancing the latchless surgical clips comprises a pusher bar for individually advancing the distal-most clip in the area of the pair of jaws, the pusher bar being longitudinally slidable in response to actuation of the handle. The pusher bar is movable between a first position wherein the distal end of the pusher bar is located proximally of the latchless surgical clip to be advanced, and a second position wherein the distal end of the pusher bar advances the latchless surgical clip to the jaw means.

The first transmission means acts on the pusher bar positioned within the endoscopic section and comprises a proximal pusher tube connected to the proximal end of the pusher bar. The first pusher tube includes mounting means for rotatably connecting the pusher bar thereto. The mounting means of the pusher tube comprises a generally circular shaped projection dimensioned for reception and engagement of at least one cooperating projection on the pusher bar.

The second transmission means acts on a channel member positioned within the endoscopic section, and comprises a proximal channel tube connected to the proximal end portion of the channel member. The channel tube includes mounting means for rotatably connecting the channel tube to the channel member. Links connect the second transmission means to a lever actuator and convert the rotational movement of the lever to linear movement of the channel tube.

The jaw means preferably comprises a jaw blade fixed to the endoscopic section and having a pair of distal spaced jaws which are resiliently movable between a closed position for closing a latchless surgical clip and an open position for reception of the latchless surgical clip. The camming means is comprised of a channel member having camming surfaces movable from a first position proximal of the jaws, and second distal position wherein the camming surfaces of the channel member move the jaws to the closed position. The channel member is connected at its proximal end to the channel tube.

The rotatable mounting means of the channel tube comprises a circumferential projection dimensioned for engaging at least one cooperating notch in the camming means. The endoscopic section is rotatable about a longitudinal axis extending relative to the frame between a plurality of click-stop settings. Further, endoscopic section is preferably adapted to provide a gaseous seal means in the form of silicone grease.

A method is also disclosed for endoscopically applying latchless surgical clips with an apparatus having a frame adapted to be gripped by hand and an endoscopic section connected to the frame and rotatable to selected positions relative to the frame, comprising storing the latchless clips in the endoscopic section, sequentially advancing a clip distally by clip advancing means positioned within the endoscopic section to a pair of jaws positioned at the distal end of the endoscopic section and opening the clip therewithin, positioning the clip adjacent body tissue to be clipped, closing the jaws about the clip while permitting the clip to close and simultaneously repositioning the clip advancing means to a position proximal of the next clip to be advanced, and releasably locking the clip advancing means in that position until released to advance the next clip.

BRIEF DESCRIPTION OF THE DRAWINGS

Preferred embodiments of the invention are described below with reference to the drawings wherein:

FIG. 3 is a plan view from above, of the distal portion of the endoscopic section of the apparatus of FIG. 1 in its initial condition;

FIG. 4 is a cross-sectional view taken along lines 4—4 of FIG. 3 illustrating the clip pusher in position to push the clip next in line to a position between the jaws of the apparatus;

FIG. 5 is a plan view of the distal portion of the apparatus with the clip now advanced and partially opened;

FIG. 6 is a cross-sectional view taken along lines 6—6 of FIG. 5 illustrating the distal portion of the apparatus in elevational view;

FIG. 7 is a plan view of the distal portion of the apparatus with the clip further advanced and in position for entry into and between the jaws;

FIG. 8 is an elevational cross-section view of the apparatus taken along lines 8—8 of FIG. 6;

FIG. 9 is a plan view of the distal portion of the apparatus with the clip further advanced and now fully positioned between the jaws and ready for closure onto body tissue;

FIG. 10 is an elevational cross-section view of the apparatus taken along lines 10—10 of FIG. 9;

FIG. 11 is a plan view of the distal portion of the apparatus with the clip now fully closed onto body tissue;

FIG. 12 is an elevational cross-sectional view of the apparatus taken along lines 12—12 of FIG. 11;

FIG. 13 is a cross-sectional view of the distal portion of the apparatus taken along lines 13—13 of FIG. 4;

FIG. 14 is a cross-sectional view of the apparatus taken along lines 14—14 of FIG. 7;

FIG. 15 is a sectional view taken along lines 15—15 of FIG. 12;

FIG. 16 is a perspective view of the clip;

FIG. 17 illustrates a surgical operation for applying clips to tubular-shaped body tissue;

FIG. 22 is a cross-sectional view taken along lines 22—22 of FIG. 19 and illustrating the trigger connection;

FIG. 23 is a cross-sectional view taken along lines 23—23 of FIG. 19 and illustrating the channel tube and pusher member;

FIG. 24 is a view taken along lines 24—24 of FIG. 19 illustrating the rack and pinion assembly; and FIG. 25 is a cross-sectional view taken along line 25—25 of FIG. 19 illustrating the lever linkages.

DETAILED DESCRIPTION OF PREFERRED EMBODIMENTS

1. Preface

In the following description it should be noted that such terms as "distal" and "proximal", "upper" and "lower", "horizontal" and "vertical", "above" and "below", are used relative to each other and do not refer to positions or orientations relative to a frame of reference external to the apparatus.

Because endoscopic procedures are more common than laparoscopic procedures, the present invention shall be discussed in terms of endoscopic procedures and apparatus. However, use herein of terms such as "endoscopic", "endoscopically" and "endoscopic portion", among others refer generally to instruments having elongated and relatively narrow operating portions for inserting into a cannula, body opening, or small wound in the skin and should not be construed to limit the present invention to an apparatus for applying surgical clips only in conjunction with an endoscopic tube. To the contrary, the present invention may find use in any procedure where access is limited to a small incision or body opening, including, but not limited to laparoscopic procedures. In addition, in the preferred embodiment of the invention the instrument is disposable. However, re-usable instruments are also contemplated.

2. Overview of the Apparatus

Figure 1:
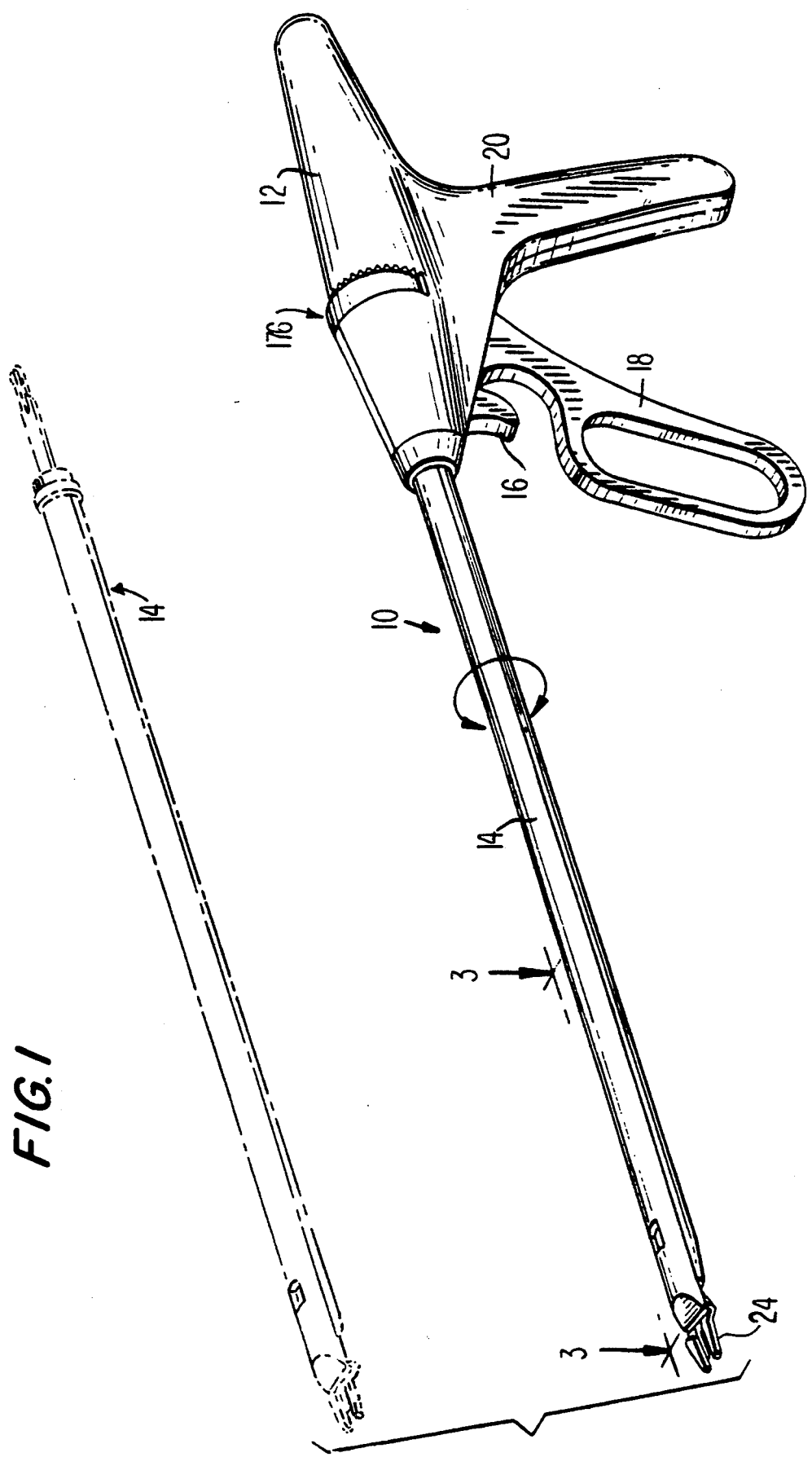
FIG. 1 is a perspective view of the disposable apparatus for placing clips in laparoscopic or endoscopic procedures constructed according to the present invention.

FIG. 1 illustrates a preferred embodiment of the apparatus of the present invention. The apparatus is preferably constructed as a disposable item of several materials as will be described. Essentially, however, two basic materials are used: a polycarbonate plastic such as LEXAN brand polycarbonate produced by General Electric Company, and stainless steel.

Briefly, the apparatus 10 includes two main sections: a handle section 12, and an endoscopic section 14 which is distal of the handle section. The endoscopic section 14 of the apparatus is rotatable with respect to the handle section 12 by turning knob 176 and is separable and replaceable with another endoscopic section.

The apparatus has two actuators. A clip pushing system, which advances a surgical clip to jaw members 24, is operated by actuation of trigger 16 by a single finger of the user's hand (e.g. the index finger). The clip closing mechanism is actuated when lever 18 is squeezed towards handle grip 202 by other fingers of the user's hand. The clip closing action of the jaws 24 is accomplished by translating longitudinal drive movement transmitted through the endoscopic section 14 to lateral motion of jaws 24, as described below.

3. The Handle Section

Figure 18:
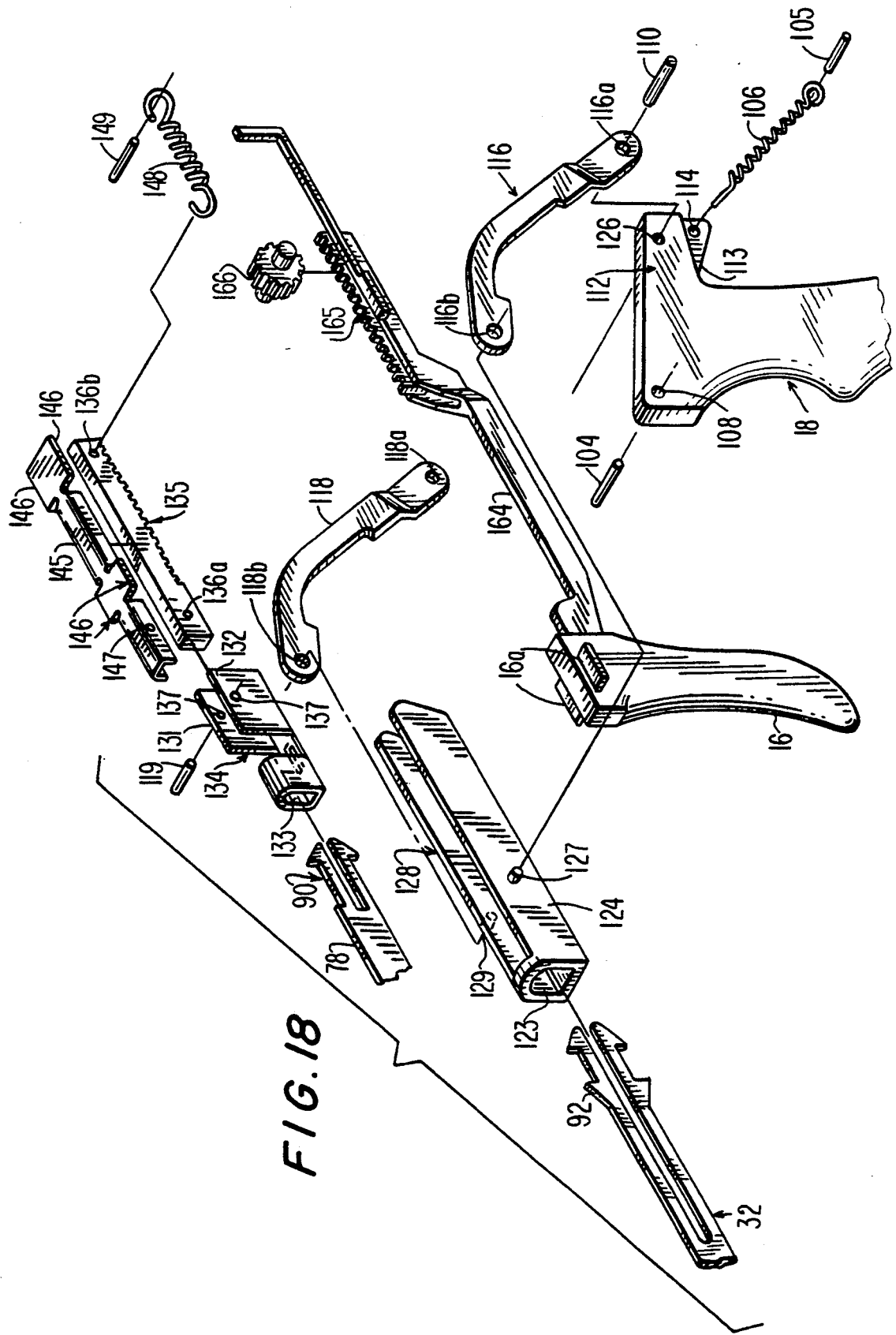
FIG. 18 is a perspective view with parts separated for purposes of illustration of the handle section of the apparatus of FIG. 1 utilized for activating the endoscopic section.
Figure 19:
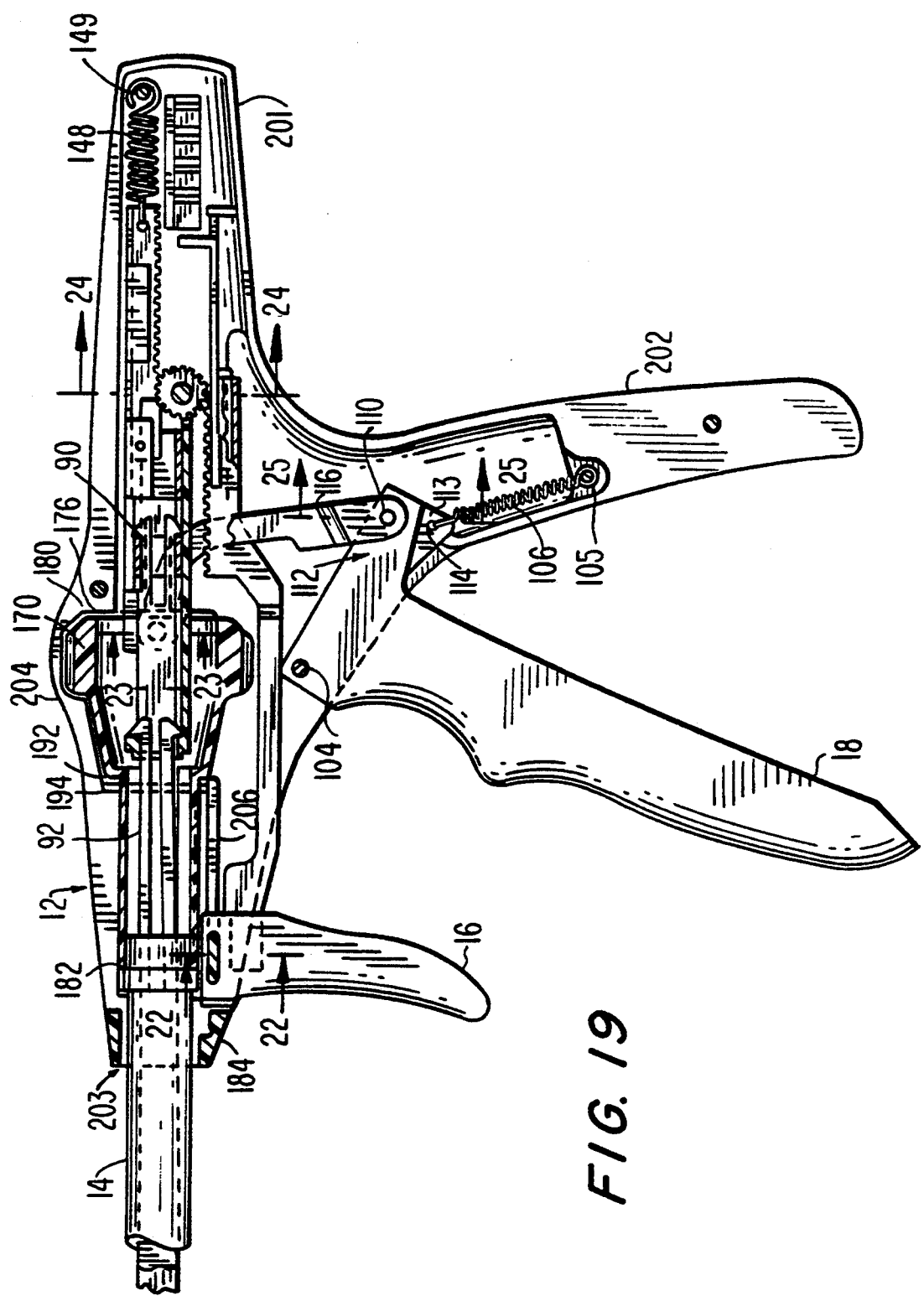
FIG. 19 is an elevational cross-sectional view of the handle of the apparatus of FIG. 1 illustrating the apparatus in its initial prefired condition.

Referring now to FIGS. 18 and 19, the handle section 12 of the apparatus is illustrated with the transmission mechanism for manually activating the endoscopic section referred to above, i.e. for advancing clips distally and crimping the clips around a blood vessel or other tubular structure. Handle section 12 includes a body 201 (FIG. 19), which houses the actuation means of the apparatus. The body portion 201 includes a handle 202 and an opening 203 for receiving the endoscopic section 14 of the apparatus. A bridge portion 204 is preferably extended over collar 170.

The body 201 is preferably fabricated in halves which may then be fastened together by fasteners such as screws or rivets. Alternatively the body halves may be ultrasonically welded or adhesively attached along their seams or by bosses and transverse rods or pins in engaging relation. The body 201 is preferably fabricated from a hard and durable plastic such as LEXAN polycarbonate material available from General Electric Co. Other rigid materials are also contemplated, especially materials capable of being molded into shape while being able to sustain the forces applied by the transmission mechanism capable of demonstrating minimal dimensional changes due to temperature or stress.

The clip loading and crimping system is divided into two separate systems as described in connection with the endoscopic section. As noted, a first system pushes the clip next in line from a row of clips to a position within a pair of clamping jaws 24 as described in connection with the endoscopic section of the apparatus. The second system closes the pair of jaws 24 around the clips to cause the clip to grip the intended artery, tissue, or other blood vessel, while simultaneously repositioning the clip pusher mechanism to push the clip next in line into position between the jaws. This procedure is repeated alternately and sequentially until all clips are spent or the surgical operation is completed.

With reference to FIGS. 18 to 25, the clip pusher and clip closing actuation mechanisms will now be described. Lever 18 is an actuator for closing the jaws 24 of the instrument and is pivotally mounted to the body 201 by means of pin 104 extending transversely to the body and disposed through aperture 108 in lever 18 (FIG. 18). The lever 18 includes rearward extension 112 which includes aperture 126 through which pin 110 extends. Pin 110 functions as a pivot for left channel link 116 and right channel link 118, which extend in a generally forward or distal direction.

Lever 18 includes depending portion 113 having aperture 114 for receiving one end of spring 106. The other end of spring 106 is attached via pin 105 to the interior of handle 202 of the body. Spring 106 biases lever 18 clockwise as seen from the instrument orientation as shown in FIG. 19. Actuation of lever 18 requires counter clockwise pivoting of the lever by the fingers of a user's hand. Thus, actuation of lever 18 is accomplished against the biasing force of spring 106.

Left and right channel links 116 and 118, respectively, each include apertures 116a and 118a, respectively, for receiving pin 110. Upper apertures 116b and 118b in the respective left and right channel links are pivotally mounted to bosses 127 and 129, respectively, of channel tube 124. Thus, actuation of lever 18 causes channel links 116 and 118 to push channel tube 124. Thus, actuation of lever 18 causes channel links 116 and 118 to push channel tube 124 distally.

Channel tube 124 is an elongated member having a distal opening 123 for receiving the proximal end of the crimping channel 32 by snap fit engagement of the legs, or prongs 92. Channel tube 124 includes a central longitudinal passage 128 for receiving pusher member 134, which is slidably disposed therein.

Figure 20:
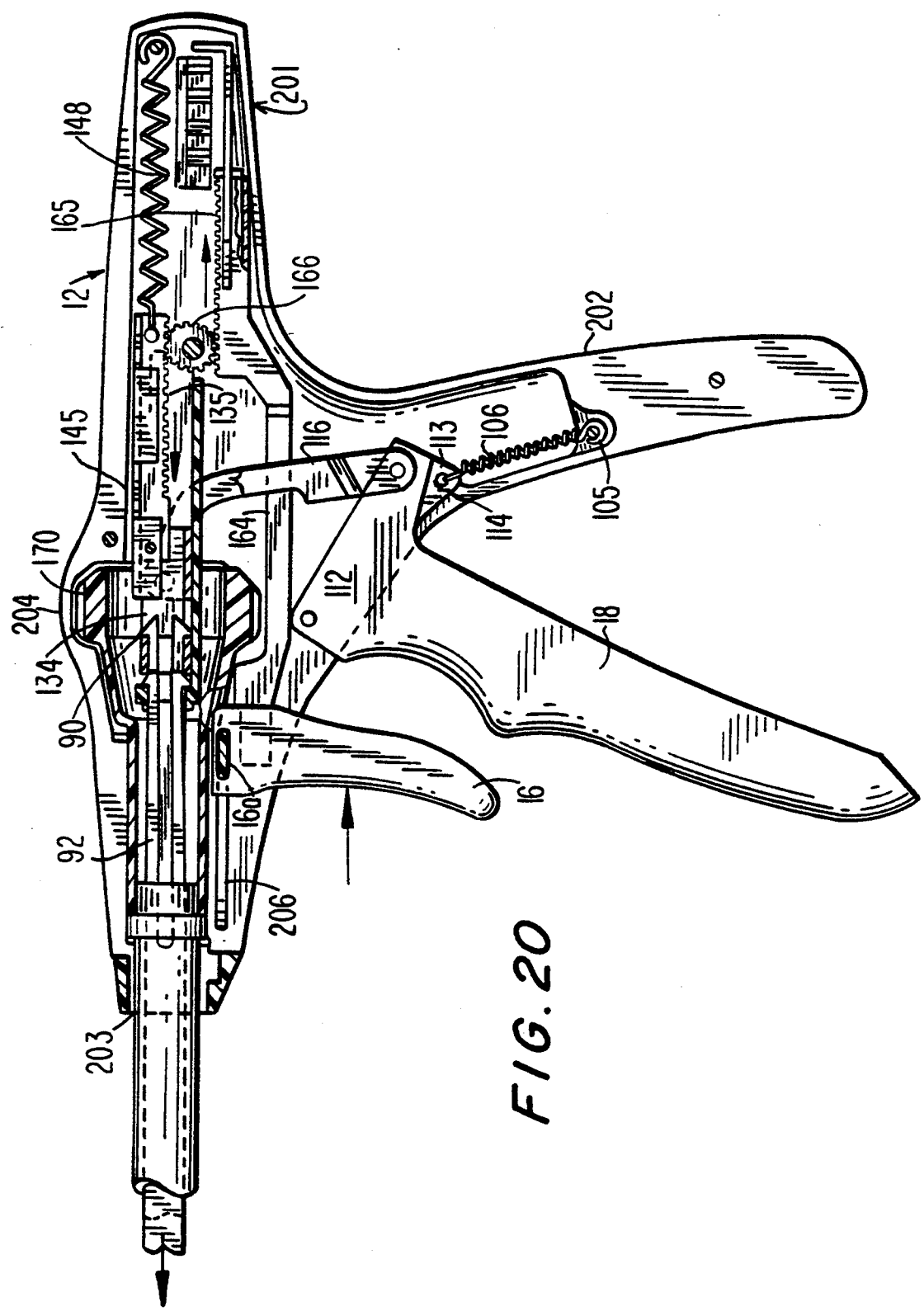
FIG. 20 is an elevational cross-sectional view of the handle of the apparatus of FIG. 1 with the trigger actuated to advance a clip to the jaws of the apparatus.

Referring again to FIGS. 18-25, trigger 16 is an actuator for advancing the clips to the instrument jaws in response to finger pressure applied by a user of the instrument. Trigger 16 includes tabs 16a which are slidably mounted in corresponding slots 206 in the interior surface of body portion 201 (FIGS. 19, 20, 22). Attached to trigger 16 is extension member 164 which includes a lower gear rack 165. Pinion gear 166 is pivotally mounted to the body 201 and is positioned above rack 165, which it cooperatively engages. Pinion gear 166 also engages upper rack 135 such that when lower rack 165 moves proximally, upper rack 135 moves distally. Upper rack 135 is fixedly mounted to rack holder 145 and possesses front and rear apertures 136a and 136b, respectively. Rear aperture 136b receives the distal end of spring 148. Front aperture 136a receives pin 119. Rack holder 145 includes flaps 146 which are slidably mounted in corresponding slots in body 201, and aperture 147 for receiving pin 119. Spring 148 is for biasing the upper rack (and the clip pushing transmission) to the proximal position. The proximal end of the spring 148 is mounted to cross pin 149, which is fitted to body 201, and the distal end of spring 148 is mounted to aperture 136b of the upper rack.

Pusher member 134 includes a distal opening 133 for receiving forked proximal end 90 of clip pusher bar 78 by snap fit engagement. Pusher member 134 also includes sides 131 and 132 defining a central passage, and apertures 137 through which pin 119 is disposed. Thus, pin 119 fastens pusher member 134, rack holder 145, and upper rack 135 by extending through apertures 137, 147 and 136a.

In operation, proximally pulling trigger actuator 16, as shown in FIG. 20, causes lower rack 165 to move proximally. Pinion gear 166 thereupon converts the proximal motion of lower rack 165 to the distal motion of upper rack 135 along with the remainder of clip pushing transmission system (rack holder 145, pusher member 134, pusher bar 78) for advancing the distalmost clip in a row of stored clips to the jaws.

When trigger 16 is released, upper rack 135 and its associated structures are biased back to their proximal position by means of spring 148 and trigger 16 is biased forward.

Figure 21:
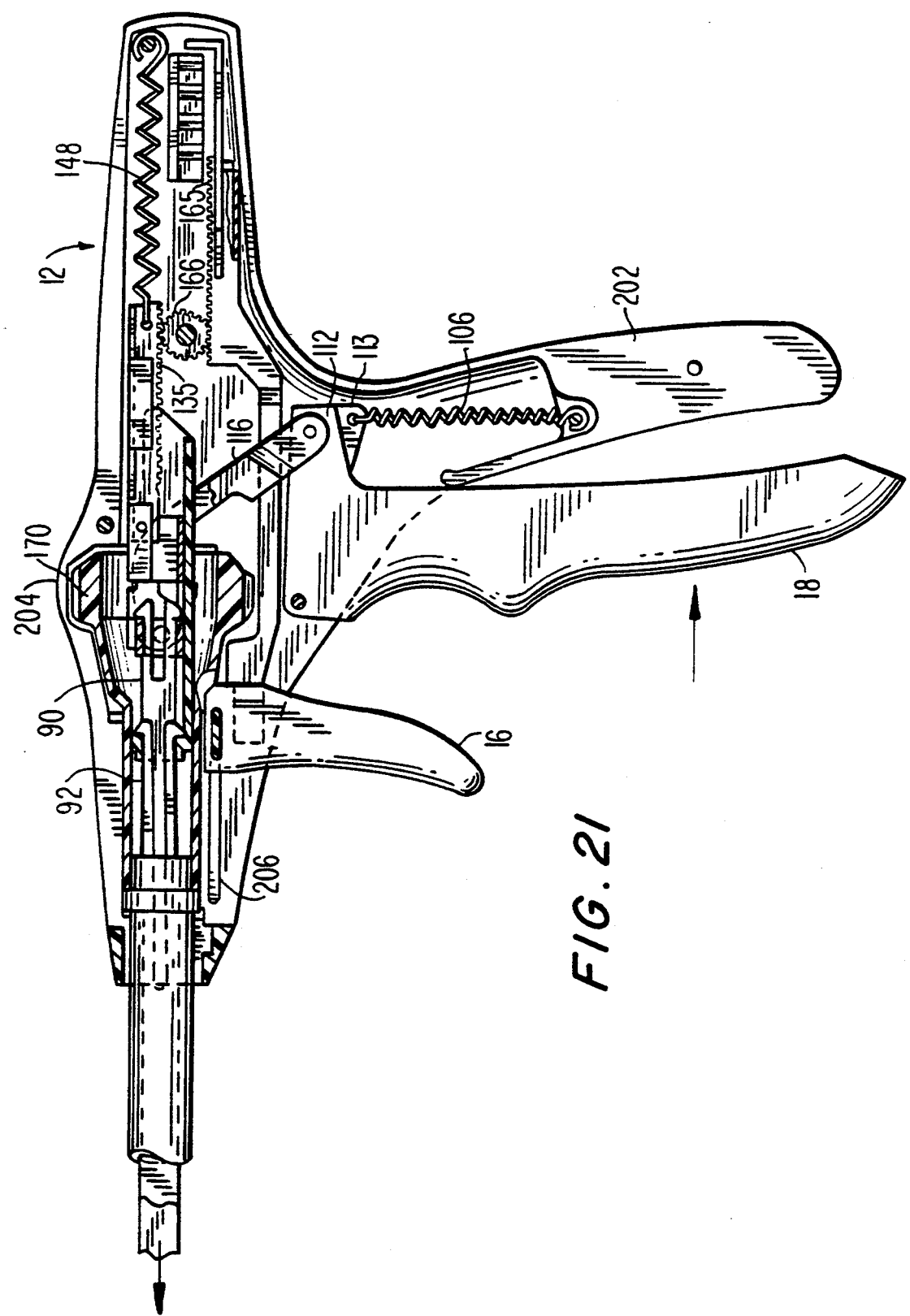
FIG. 21 is an elevational cross-sectional view of the handle section of the apparatus illustrating the actuation of the lever to close the instrument jaws.

Referring to FIG. 21, squeezing lever 18 towards handle 202 causes pivotal movement of channel links 116 and 118 which translates to forward longitudinal motion of channel tube 124.

4. The Rotational Linkage

Referring now to FIG. 3 in conjunction with FIG. 2 and FIGS. 19 and 18a, the feature relating to the rotatable endoscopic section will be described. Rotating collar 170 is constructed of the same material as the handle, i.e., preferably a polycarbonate material such as LEXAN brand material. This collar 170 includes a distal cylindrical nose section 172 and a proximal barrel section 174. The proximal face of the barrel section 174 preferably includes a plurality of proximally extending teeth 176 positioned circumferentially about the proximal face of the barrel section, and the cylindrical nose section 172 includes an inwardly extending rib 178 at the distal end for engaging groove 15a of upper endoscopic cartridge half 15. In the assembled condition, the cylindrical nose section rests within the cylindrical distal bore 182 of the distal end of the handle and nose piece 184 is fitted over the distal cylindrical end of the handle 12 as shown, for example, in FIGS. 19 and 20. Bearing washer 186 and spring washers 188, 190 are positioned between shoulder 192 of collar 170 and shoulder 194 formed in the handle body to bias the rotatable collar in the proximal direction causing tooth 180 on the handle body to engage the teeth 176 of the collar 170 to thereby fix the rotatable orientation of the collar. When the surgeon desires to change the angular orientation of the endoscopic section, the collar 170 is merely pushed distally to disengage tooth 180 to free the collar and permit rotation relative to the handle body. Such rotation of the collar is clearly permitted by the fact that the cylindrical nose section of the collar is fit snugly within the corresponding cylindrical distal section 182 of the handle. Except when the tooth 180 of the handle body is engaged with teeth 176 of collar 170, the collar is otherwise free to rotate within the handle.

Figure 2:
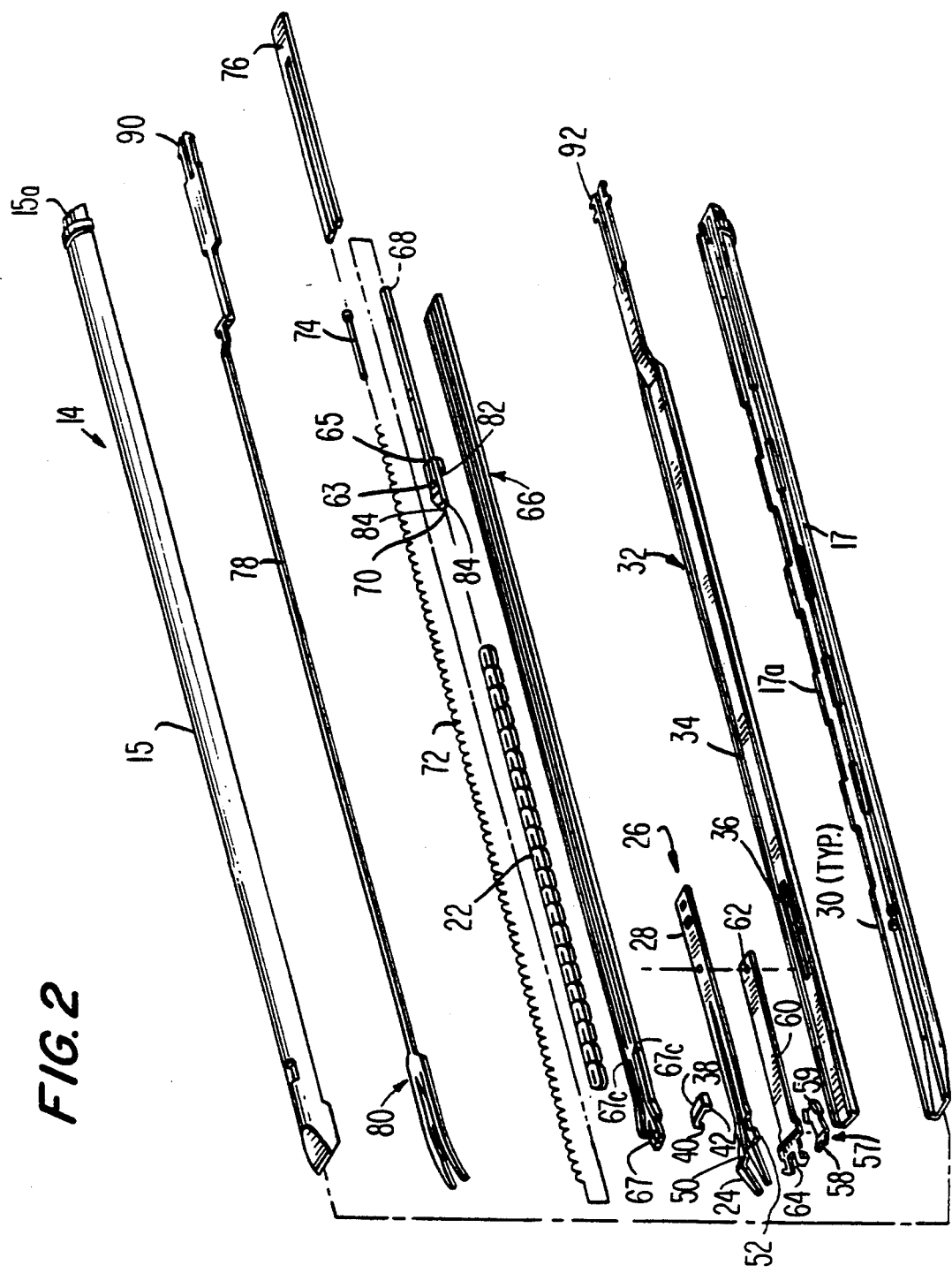
FIG. 2 is a perspective view with parts separated for purposes of illustration of the endoscopic section of the apparatus of FIG. 1.
Figure 18A:
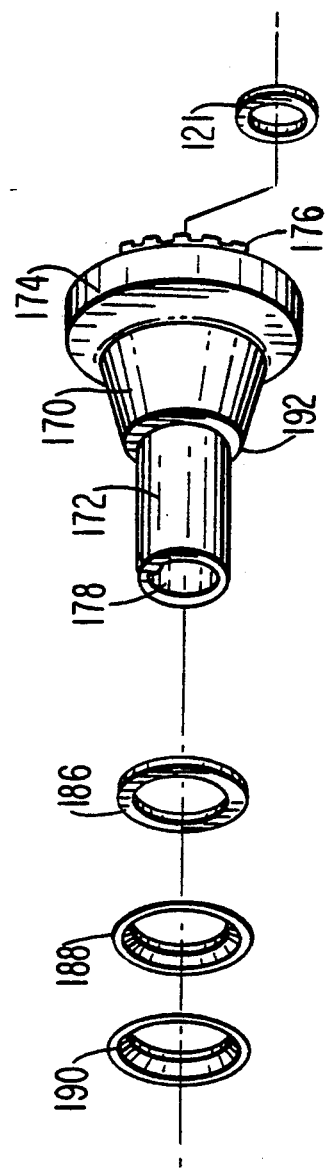
FIG. 18a is a perspective view of the rotatable collar.

Referring now to FIG. 2 in conjunction with FIGS. 1, 18a and 19, the distal cylindrical section 172 of collar 170 includes a distal cylindrical opening dimensioned to receive the endoscopic cartridge formed of upper half 15 and lower half 17 of endoscopic section 14, with distally positioned tooth 178 of collar 170 positioned within longitudinally extending groove 15a of upper cartridge half 15 to cause the cartridge to rotate with the collar 170. Similarly, the proximal legs 90 of clip pusher bar 178 are permitted to rotate within the distal end portion 133 of pusher tube 134 and the proximal legs 92 of the crimping channel 32 are permitted to rotate within the distal end portion 123 of channel tube 124. Thus, the entire endoscopic section may be selectively rotated by the surgeon by simply pushing collar 170 in the distal direction sufficient to disengage tooth 180 on the handle body and by rotating the collar 170 until the endoscopic section reaches the desired angular orientation. Thereafter, by merely releasing the collar the bias of spring washers 190, 188, causes the collar to move proximally, such that tooth 180 on the handle body engages the appropriate teeth 176 on the collar 170 to lock the position of the collar and the endoscopic section.

5. The Latchless Clip

Unlike the latching, or locking, surgical clips of the prior art, the latchless clip of the present invention provides a tissue clamping force which is self-adjusting for a variety of tissue types and tissue thicknesses. The ability of the latchless surgical clip to readily accommodate different tissue clamping situations with no appreciable risk of tissue injury represents a significant advantage over the latching, or locking, surgical clips of the prior art.

Referring to FIG. 16, latchless surgical clip 22 is provided as a single molded substantially planar polymeric clip body possessing two legs 44 joined at one end through hinge back region 45. Latchless surgical clip 22 is molded, e.g., by injection molding, in an open or pre-application configuration, i.e., with legs 44 spaced apart from each other. As molded, polymeric latchless clip 10 is substantially amorphous, i.e., the molded polymer exhibits less than 10% crystallinity. After molding in this open configuration, latchless clip 10 is treated so as to impart a spring-back property to hinge region 14.

A preferred post-molding clip treatment process of the latchless clip 22 shown in FIG. 16 involves heating the clip 22 to a temperature which permits legs 44 to be moved or deflected into a second position which is different from the as-molded position. Inasmuch as molded clip 22 is substantially amorphous, clip 22 is typically heated to a temperature at or above the glass transition temperature of the polymeric material from which it is fabricated. Once at or above its glass transition temperature, the substantially amorphous polymer is soft or rubbery, thereby facilitating movement of legs 44 to a second position. Once deflected to this second position, clip 10 is further heated to a temperature at which crystallization of the polymer commences. In order to achieve the desired spring back property in hinge back portion 45, polymeric clip 22 is typically maintained at a crystallization temperature for a time sufficient to develop at least 20% crystallinity preferably at least 30% crystallinity, and most preferably at least 40% crystallinity.

The post-molding treatment of clip 22 typically results in a minor degree of shrinkage of the clip body, and typically causes a rounding of any sharp edges present on clip body. However, neither the shrinkage nor the rounding impinges upon the clinical efficacy of the device and, indeed, the rounding of sharp edges is generally desired to reduce the likelihood of tissue puncture or laceration upon clip application.

After sufficient crystallization is accomplished, clip 22 is cooled to ambient temperature. Clip 22 remains oriented in its second position absent an external biasing force away from said second position. The above-described post-molding treatment imparts an elastic spring back property to hinge region 45 such that when a biasing force is applied to legs 44, e.g., a force biasing legs 44 away from each other, and then withdrawn, legs 44 spring back toward each other, i.e., to or toward their second (pre-spread) positions.

The flexural strength of the latchless clip of the invention may be increased through a post-flexing process after the clip has been subject to a post-molding treatment to achieve the desired degree of crystallinity and of spring back property in the hinge region. Post-flexing involves repeatedly and temporarily biasing the legs apart through application of a temporary biasing force at an elevated temperature, e.g., 30°–50° C. Such post-flexing treatment has been found to lessen the internal stresses experienced by the clip when being applied to tissue at ambient temperature.

A wide variety of polymeric materials may be used to fabricate latchless clip 22 of the present invention. The principal requirement of the polymer is that it develop sufficient crystallinity upon movement to a second position to impart a sufficient spring back force to hinge region 45. Of course, the required spring back force will vary depending on the intended application of clip 22. Among the materials which are suitable for the manufacture of clip 10 are non-bioabsorbable polymers such as the polyesters, polyamides, polycarbonates, polyvinyl chloride, polysulfones, and polypropylenes. Suitable bioabsorbable polymers include homopolymers and copolymers of lactide, glycolide, trimethylene carbonate, caprolactone, and p-dioxanone, and blends thereof. A preferred bioabsorbable polymer is a copolymer derived from approximately 80 to 95 weight percent glycolide and 5 to 20 weight percent lactide.

In one preferred embodiment of the present invention, each leg 44 possesses upper and lower parallel rows of spaced-apart staggered tooth-like projections 46, which cooperatively engage the corresponding rows of projections on the other leg. Although the projections are shown to be substantially rectangular in shape, clearly projections of other configurations and sizes could be utilized. Additionally, a smaller or greater number of projections than are shown may be utilized to achieve the interfitting arrangement of the projections to enhance clip securement. It is also contemplated that spaced projections may be limited to the tissue clamping surface of one leg, these projections being adapted to cooperate with the tissue clamping surface of the opposing leg to effectively secure clip 22 to tissue.

Latchless clip 22 is applied by a device such as the one described herein, which possesses means for temporarily resiliently biasing legs 44 apart by clip opening means and placing the open clip into position at a desired tissue site. Clip 22 may be provided with upwardly extending pins 49a and an instrument can be utilized which grasps the closed clip in its jaws and, following engagement with pins 49a resiliently biases the legs apart the required amount to allow application of the clip to the desired tissue site, e.g., by directing a pushing force against the pusher post 48, which brings the clip into engagement with the body tissue. Once applied to the site, the biasing force is withdrawn whereupon legs 44 return to the closed, or tissue clamping, configuration thereby providing effective hemostasis.

Referring once again to FIG. 16, post 48 extends upward from the center of the proximal portion 45 and serves as a pusher post. Post 48 is engaged by clip pusher 78 for advancing clip 22 when clip pusher 78 is moved distally. Lower projection 43 engages slot 67d of the track 66 to serve as a guide for proper orientation of clip 22 as it is advanced. Posts extend upward and downward from the legs 44. Upper posts 49a engage the clip pusher 78 for advancing the clip 22, and lower posts 49b serve as spreader posts for interaction with the clip opening means, which comprises a track portion having at least one, and preferably two camming surfaces 67a and 67b positioned such that upon distal advancing of the clips the lower posts 49b contact the camming surfaces and are laterally moved to a more spaced apart configuration. As lower posts 49b cam against surfaces 67a and 67b (as explained below with reference to FIG. 3) the legs 44 spread apart. Notches 47 extend along the outside surface of legs 44.

The clips of the present invention may be constructed in various sizes according to their intended function. For example, for a latchless clip to be used in hemostatically occluding a blood vessel, a length of about 1 cm, a width of about 5 mm and vessel clamping surface of about 5 mm in length are typical. The dimensions may be reduced as appropriate, e.g., by about 50%, for microsurgical applications. Conversely, the dimensions may be increased as appropriate, e.g., by about 100% for female sterilization, in which oviduct occlusion is desired. For male sterilization, occlusion of the vas deferens may be accomplished with smaller clips. The clip can be molded in various colors to increase color contrast with surrounding tissue and/or to facilitate identification of the size of the clip.

The clip body, particularly the hinge region and legs, of the latchless surgical clip of the invention possesses sufficient resilience to permit the clip legs to be deflected apart an appropriate distance to allow the clip to be easily and efficiently placed on or around the desired tissue. Generally, the clip body is sufficiently resilient to permit the legs to be deflected to a position wherein the legs are separated by an angle of from 15° to 50°, and more typically an angle of from 20° to 35°. This angle of maximum deflection will depend on such factors as the polymeric material, the degree of crystallinity of the clip body after the 15 post-molding treatment, the physical dimensions of the clip body, the presence of cored sections, and whether the clip body has experienced post-flexing. The angle of maximum deflection may correspond to, but is not necessarily restricted to, the angular opening of the legs in the as-molded configuration.

The hinge region also possesses a sufficient spring back force to bring the legs toward each other (once the external biasing force is removed from the legs) to apply an effective tissue clamping force to the tissue. The tissue clamping force which the clip must deliver will depend on such factors as the type and size of the tissue to which it is to be applied. Typically, in order for the clip to effectively occlude a tissue structure, e.g., a blood vessel, the clip should apply a residual force of about 0.5–1.0 psi once placed on the tissue structure. Once placed on tissue, the hemostatic latchless clip of the invention maintains that position for a period of time sufficient to permit hemostasis to take place, i.e., maintains its strength in vivo so as to withstand the internal pressure which is trying to force the tissue structure back open until the natural, permanent sealing of the tissue structure is complete.

6. The Endoscopic Section

Referring now to FIG. 2 in conjunction with FIGS. 3 to 14 and FIG. 1, the endoscopic section 14 of the apparatus will now be described. The endoscopic section 14 is preferably housed in a non-removable cartridge formed of upper half 15 and lower half 17. Each half section is formed of a material capable of withstanding the stresses applied to the inner working compartments without deformation or compromise of precision. A polycarbonate material such as LEXAN brand material marketed by General Electric Corporation has been found to satisfy the requisite strength and deformation requirements. Other suitable materials may be used. If desired, the cartridge can be constructed to be removable from the handle.

The lower housing half section 17 includes upstanding tabs 17a and the upper housing half section 15 includes correspondingly positioned slots (not shown) which are configured and dimensioned to receive tabs 17a such that the two half sections may be attached by ultrasonic welding techniques. Preferably, the slots are dimensioned to receive the tabs 17a in interference relation to assist securement of the half portions together. Alternatively, the half sections may be adhesively attached. Further, upper half section 15 includes longitudinally extending slots 15a which receive correspondingly dimensioned ribs in the collar of the handle section to facilitate rotation of the endoscopic section with the collar. Referring once again to FIG. 2, a plurality of U-shaped latchless clips 22 are positioned within the housing for movement in the distal direction in preparation for the clamping procedures. The clips 22 are aligned in a row as shown, with the leg portions facing distally. A jaw blade 26 is positioned at the distal end and includes a pair of jaws 24 for reception of each clip. Although the clips 22 are resilient and automatically snap back into a closed position after being released from an open position, it should be remembered that during use the clips will have body tissue positioned between the clamping surfaces of the legs. Therefore, it is desirable to provide additional closing force to facilitate complete clamping of the body tissue by the clip. This additional force is applied to the outer edges of the clip legs by jaws 24.

One feature of the present invention is to bias the surgical clips toward the distal direction and to sequentially advance each clip into the jaws after the jaws have been positioned about an artery. Thereafter, the jaws are closed and both legs of the "U" shaped clip are brought together to sufficiently close the artery as shown in FIGS. 11, 12, and 16.

The jaw blade 26 is fabricated of a material having sufficient resilience such that clamping of the distal pair of jaws 24 toward each other to close a clip therebetween will be followed by return of the jaws to their original position upon release of the clamping forces. Stainless steel has been found to be a preferred material capable not only of withstanding the requisite number of clamping cycles without adverse effect, but also of being suitably sterilized. Furthermore, jaw blade 26 includes one or more square shaped apertures 28 dimensioned to receive three correspondingly shaped pins 30 molded into the lower body half section 17 of the housing to position the jaw blade 26 with respect to the body.

Referring further to FIG. 2, crimping channel 32 is dimensioned and positioned for slidable movement within the body of the housing and has upraised side walls 34 along the sides and further has a slot 36 at the distal end for reception of square pins 30. The width of the slot 36 of crimping channel 32 is sufficient to receive the pins 30 to maintain relative alignment between the jaw blade 26 and the pins 30. A channel bracket 38, also preferably of stainless steel, is positioned atop the jaw blade and defines two downwardly extending side walls 40, 42 positioned to be welded to the distal portions of correspondingly positioned and dimensioned upwardly extending side walls 34 of crimping channel 32. It will be appreciated that the crimping channel 32 forms with channel bracket 38, a rectangular slidable housing surrounding the jaws 24 of jaw blade 26. Moreover, since the jaw members 24 are formed of outwardly tapered side walls having camming surfaces 50, 52, distal movement of the crimping channel 32 will cause inward movement of the jaw members, while proximal movement of the crimping channel will result in corresponding proximal movement of channel bracket 38 thereby relieving the jaw members 24 of the crimping forces and permitting the jaw members to resiliently open.

Referring now to FIGS. 2 and 3, jaw members 24 include inner edges 54, 56 dimensioned to receive a clip 22 therebetween for clipping a body portion. Tissue stop plate 60 shown in FIG. 2, is positioned between jaw blade 26 and crimping channel 32 and includes aperture 62 at the proximal end portion for reception of an appropriate pin (not shown) which extends through the jaw blade 26 and tissue stop plate 60 to maintain alignment of the jaw blade 26 and the tissue stop plate 60 when these components are welded together. At the distal portion of the tissue stop plate a tab 64 is oriented at approximately the same downward angle as the jaws 24 for alignment therewith arid includes an arcuate cut-out portion as shown, dimensioned to snugly receive an artery for locating and positioning the artery in the precise area within the jaw blades as required for applying a clip to the artery with predetermined precision. The tissue stop plate is preferably fabricated of a thin stainless steel sheet material.

Support plate 57 is positioned underneath the tissue stop plate 60 and includes an upwardly bending distal section 58 which supports the tab 64 at the distal end of tissue stop plate 60, and proximal walls 59 which extend partially around the outer edges of the jaws 24.

Referring further to FIG. 2, track member 66 is appropriately dimensioned to rest atop the clip clamping mechanism described hereinabove, and supports the row of clips 22. Proximally of clips 22 is positioned a clip follower 68 which is "U" shaped at the distal end to snugly engage and advance the clips under the action of clip feed spring 72, the distal end of which is connected to the proximal end of clip follower 68 and the proximal end of which is mounted to pin 74. Pin 74 is in turn connected to pusher bar support 76 while clip pusher bar 78 is positioned for slidable movement thereon between a proximal position and a distal-most position. Clip pusher 78 includes forked nose section 80 and a depending catch 87 (see FIGS. 6 and 8) for engaging the upright rear post 48 of the clip. When upright rear post 48 of the next clip 22 is engaged by catch 87 in the distal nose 80 of clip pusher 78, distal movement of the clip pusher 78 advances the clip between the edges 54, 56 of jaws 24 which engage slots 47 along the sides of the clip 22. As clip 22 advances, lower spreader posts 49b cam against the distal wedge surfaces 67a and 67b of spreader portion 67 of track 66. This action forces open clip legs 44 from an initially closed position to an open position. When the clip moves beyond the distal edge of the spreader portion 67 of the track 66 the lower spreader posts 49b no longer contact the distal wedge surfaces 67a and 67b, thereby permitting the clip legs to close. The clip legs close due to the resilience of the material from which the clip is fabricated with the assistance of the closing force applied by jaws 24.

When all the clips have been applied, clip follower 68 advances to ridges 67c of track member 66. Slots 84 on the sides of the distal portion 70 of clip follower 68 engage ridges 67c and the follower distal portion 70 is stopped when stopping shoulder 82 abuts the proximal edge of ridges 67c.

Referring again to FIG. 2, by sliding clip pusher bar 78 between the proximal and distal positions, the clip pusher bar may be alternately positioned with nose 80 behind each successive clip, and thereafter advancing the clip into the jaws 24 of jaw blade 26 by pusher mechanism in handle section 12 which will be described. The connection between the mechanism in the handle 12 is made with the proximal end portion 90 of clip pusher 78 which extends into the handle section. Further, the connection between the appropriate link of handle 12 with the crimping mechanism of jaw blades 24 is made with the proximal end portion 92 of crimping channel 32 as will be described. The precise action of the handle 12 and its inner mechanism is such that proximal force applied to trigger 16 causes clip pusher 78 to push the next clip 22 into the jaws 24 while simultaneously releasing the crimping channel 32 to the "ready" position for crimping the clip. Next, the operator squeezes handle 18 toward hand grip 20 which causes crimping channel 32 to move distally to crimp the clip positioned within jaws 24, while simultaneously moving clip pusher 18 proximally in position to push the next clip 22 into the jaws 24. These movements are alternately repeated until the last clip 22 is spent.

7. Operating Sequence

A. Handle Section

Referring now to FIGS. 19-22, the clip advancing and jaw squeezing mechanisms are shown in various stages of the operation. FIG. 19 is an elevational cross-sectional view of the handle 12 of the apparatus, illustrating the pusher tube 134 in the proximal-most position corresponding to the position of the pusher bar 78 shown in FIG. 4, i.e., with the nose 80 just proximal of the next clip 22 in readiness to advance the clip distally into the jaws 24. Additionally, with pusher tube in the proximal position, downwardly extending pin 158 has moved out of engagement with latch 150 thereby permitting tongue 156 to enter the aperture of channel latch plate 146 thus preventing any distal movement of channel tube 124. This condition locks handle 18 in the distal position whereby squeezing the handle toward hand grip 20 is prevented.

Referring now to FIG. 20, there is shown a cross-sectional view of the handle 12 of the apparatus with the pusher tube in the distal-most position corresponding to the position of pusher bar 78 as shown in FIG. 10, i.e., with the clip 22 advanced distally into the jaws 24 of jaw blade 26 As can be seen further in FIG. 20, the distal position of pusher tube 134 has now resulted in release of tongue 156 of latch plate 150 from the aperture of channel latch plate 146 in the bottom wall of channel tube 124 thereby permitting advancement of channel tube 124 and crimping channel 32 distally to squeeze jaws 24 in conjunction with channel bracket 38.

Referring now to FIG. 21, a cross-sectional view of the handle 12 is shown after the crimping action has taken place on clip 22 positioned within jaws 24. The position of the components shown in FIG. 21 corresponds to the position of the jaws shown in FIG. 11, i.e., in the clamped position about clip 22. In the cross-section shown in FIG. 21, the pusher tube 134 is in the proximal-most position and the channel tube is in the distal-most position such that crimping channel 32 and channel bracket 40 are in the distal-most position.

Referring to FIG. 22, a cross-sectional view of the handle 20 is shown after the last clip 22 has been spent.

Referring once again to FIG. 18 in conjunction with FIGS. 19-22, lost motion spring 210 is shown having transverse arms 212 and tab 214. Spring 210 provides bias force on pusher links 120, 122 such that squeezing action on handle 18 maximizes proximal movement of pusher tube 134. Thus, partially closing the jaws 24 of jaw blade 26 will cause pusher tube 134 to move sufficiently proximal to make certain that pusher bar 78 has moved proximally of the next clip 22. Without such movement it may be possible for the surgeon to squeeze the jaws, not fully appreciating that the pusher bar 78 has not moved to a position proximal of the next clip 22. This proximal movement of the pusher bar is thus assisted by lost motion spring 210 which maximizes the repositioning movement of the pusher bar 78 behind the next clip whether the jaws are squeezed fully or partially. In particular, the proximal bias provided by spring 210 on pusher links 120, 122 maximizes the movement of the pusher tube 134 in relation to the movement of handle 18 by maintaining pusher links: 120, 122 in their proximal-most positions prior to squeezing the handle 18. This maximum proximal movement of pusher links 120, 122 in turn results in proximal movement of pusher tube sufficient to engage tongue 162 of release spring 160 thus making certain that pusher bar 178 is repositioned sufficiently proximally to advance the next clip 22 into the jaw members 24.

B. The Endoscopic Portion

Referring now to FIGS. 3 to 10, the operation of the endoscopic portion of the instrument is shown. More particularly, FIGS. 3 and 4 illustrate the initial condition of the instrument. The latchless clip follower 68, biased by spring 72, urges latchless clips 22 distally. Clip pusher 78 with forked nose 80 and catch 87 is positioned proximal to the distal-most clip. Tissue 200 to be clipped is located between jaws 24 and abuts tab 64 of tissue stop 60. The distal end 67 of clip track 68 possesses inclined camming surfaces 67a and 67b for contacting the upright leg posts 49 of the latchless clip 22. A central alignment slot 67d receives depending alignment post 43 of the latchless clip 22 and maintains the clip in alignment as it is advanced distally. FIG. 13 shows a sectional view of the distal portion of the apparatus as indicated.

Referring now to FIGS. 5 and 6, as the clip 22 is advanced, spreader leg posts 49b cam against surfaces 67a and 67b thereby opening legs 44 of the clip 22. Depending alignment post 43 rides in slot 67d.

As shown in FIGS. 7, 8, and 14, clip 22 is advanced further and the clip legs 44 are fully opened. The clip begins to enter the jaws 24 and the edges 54 and 56 of the jaws engage side slots 47 of the clip to maintain proper alignment. Clip 22 is advanced fully into the jaws 24 and is positioned for application to tissue 200 as shown in FIGS. 9 and 10.

Referring now to FIGS. 11 and 12, the clip closing mechanism is activated, as explained above, and jaws 24 of the instrument are closed, thereby closing latchless clip 22 around tissue 200, as illustrated in FIG. 15. The latchless clip 22 remains closed. Hence, when the jaws 24 reopen, clip 22 is released from the jaws 24.

An illustrative example of an operation which may be performed endoscopically on body tissue is shown in FIG. 17, wherein clip applier 10 applies a series of latchless clips 22 to body tissue 200.

What is claimed is:

1. An apparatus for endoscopic application of surgical clips to body tissue, which comprises:
   a) a frame,
   b) endoscopic means of generally elongated configuration defining a longitudinal axis and connected to said frame and extending distally therefrom, said endoscopic means including a tubular housing defining an internal passage and having a distal end portion, and further including:
      (i) means for storing a plurality of surgical clips in the internal passage of said tubular housing and a plurality of surgical clips stored in said storing means, each of said surgical clips possessing a pair of legs which are movable between a first position wherein said legs are in relatively close proximity with each other, a second open position wherein said legs are relatively spaced apart from each other, and a third closed position wherein said legs are in relatively close engaged relation with tissue gripped therebetween, said legs being resiliently biased toward said first position, said surgical clips being stored in said storing means in said first position,
      (ii) clip opening means located in the internal passage of said tubular housing for moving said surgical clip legs from said first position to said second open position,
      (iii) clip advancing means movable within the interior passage of said tubular housing for individually distally advancing said surgical clips to a location wherein said clips are permitted to at least partially surround body tissue when said clip legs are in said second open position; and
      (iv) means positioned at said distal end portion of said tubular housing for moving said clip legs to said third position to effect closure of said surgical clips at least sufficient to grip the body tissue.

2. The apparatus of claim 1, wherein said surgical clip legs possess opposing tissue clamping surfaces and tissue clamping means on said tissue clamping surfaces, said tissue clamping means of one leg being cooperatively engageable with said tissue clamping means of the other leg to impart a tissue clamping force to body tissue positioned therebetween.

3. The apparatus of claim 1, wherein said surgical clip includes at least one projection on each of said legs.

4. The apparatus of claim 3, wherein said clip opening means comprises a track portion having at least one camming surface positioned such that upon distal advancing of said clips said projections contact said camming surface and are laterally moved to a more spaced apart configuration.

5. The apparatus of claim 1, wherein said surgical clips each have at least one projection for engagement by said advancing means.

6. The apparatus of claim 5, wherein said clip advancing means comprises a fork shaped distal end portion for engaging said projection of the clip.

7. The apparatus of claim 1, wherein said surgical clips are stored in said clip storing means in a row aligned with the longitudinal axis of the instrument.

8. The apparatus of claim 1, wherein said means for effecting closure of the surgical clip comprises jaw means positioned at the distal end of the endoscopic means.

9. The apparatus of claim 8, wherein said clip advancing means advances the surgical clips to a position between said jaw means for positioning adjacent to the body tissue to be clipped.

10. The apparatus according to claim 9, wherein said frame comprises an instrument body and an actuating handle mounted to said instrument body.

11. The apparatus according to claim 10, wherein said frame contains first transmission means for linearly transferring motion from said actuating handle to said clip advancing means.

12. The apparatus according to claim 11, wherein said frame contains second transmission means for linearly transferring motion from said actuating handle to said jaw closing means.

13. The apparatus according to claim 11, wherein said endoscopic section is rotatable independent of said handle.

14. The apparatus according to claim 11, further comprising means for locking said handle such that after actuating said handle to close said jaws, said handle cannot be actuated unless said locking means is released.

15. The apparatus according to claim 14, wherein said handle locking means comprises a first resilient catch movable in response to actuation of said handle from an unlocked position to a locked position wherein first transmission means is advanced and locked, release means adapted to release said first resilient catch, said first resilient catch being returnable to the unlocked position in response to actuation of said release means, and a second resilient catch movable in response to actuation of said handle from an unlocked position to a locked position wherein it engages and locks second transmission means, said second resilient catch being resiliently returnable to the unlocked position in response to the release of said resilient catch.

16. The apparatus according to claim 8, wherein said jaw means comprises a pair of jaws positioned in spaced relation and configured and dimensioned for reception of a surgical clip therebetween, said jaws each having a clip contacting edge adapted to engage a corresponding notch on the outer edge of the clip, said jaws being resiliently movable toward and away from each other in response to longitudinal movement of a camming means between a proximal position and a distal position.

17. The apparatus according to claim 16, wherein said camming means comprises a channel member slidably mounted within said endoscopic section and longitudinally movable in response to actuation of said handle, said channel member having at least two distal camming surfaces for biasing the jaws into said closed position.

18. The apparatus according to claim 1, wherein said means for storing surgical clips comprises a track for holding a longitudinal array of surgical clips, and spring means located proximal to the array of surgical clips for biasing said surgical clips toward the distal direction.

19. The apparatus according to claim 18, further comprising a clip follower and a clip track positioned between said jaw means and said clip follower.

20. The apparatus according to claim 1, wherein said means for advancing the surgical clips comprises a pusher bar for advancing the distal-most clip into said means for moving said clip legs to said third position, said pusher bar being longitudinally slidable in response to actuation of said handle.

21. The apparatus according to claim 1, wherein said endoscopic section includes a gaseous seal means.

22. An apparatus for endoscopic application of surgical clips to body tissue, which comprises:
a) a frame configured and dimensioned for manual gripping,
b) an endoscopic shaft of generally elongated configuration defining a longitudinal axis and connected to said frame and extending distally therefrom, said endoscopic shaft including a tubular housing defining an internal passage and having a distal end portion, and further including:
(i) means for storing a plurality of surgical clips in the internal passage of said tubular housing and a plurality of surgical clips stored in said storing means, each of said surgical clips possessing a pair of legs which are movable between a first position wherein said legs are in relatively close proximity with each other, a second open position wherein said legs are relatively spaced apart from each other, and a third closed position wherein said legs are in relatively close engaged relation with tissue gripped therebetween, said legs being resiliently biased toward said first position, said surgical clips being stored in said storing means in said first position,
(ii) clip opening means located in the internal passage of said tubular housing for moving said surgical clip legs from said first position to said second open position,
(iii) clip advancing means movable within the interior passage of said tubular housing for individually distally advancing said surgical clips to a location wherein said clips are permitted to at least partially surround body tissue when said clip legs are in said second open position; and
(iv) means positioned at said distal end portion of said tubular housing for moving said clip legs to said third position to effect closure of said surgical clips at least sufficient to grip the body tissue.

23. A disposable apparatus for endoscopic application of latchless surgical clips to body tissue, said clips each having a pair of legs normally biased toward a first position wherein said legs are in relatively close proximity with each other, and resiliently movable toward a second open position which comprises:
a) a frame adapted to be gripped by hand;
b) an elongated endoscopic section connected to said frame, said endoscopic section comprising a tubular housing with a distal end portion and further including:
i) means for storing a plurality of latchless clips in the interior of said tubular housing;
ii) a pair of jaws at the distal end portion of said tubular housing, said jaws being configured and dimensioned for reception and clamping of said latchless surgical clips;

iii) means extending through the interior of said tubular housing for advancing said latchless surgical clips into said jaws;

iv) means located in said tubular housing for causing said legs to move toward said open position to facilitate positioning of said clip about body tissue to be clipped; and v) means for moving said jaws toward each other for closing a clip positioned therebetween.

24. A method for endoscopically applying latchless surgical clips with an apparatus having a frame adapted to be gripped by hand and an endoscopic section connected to said frame, comprising:

a) storing a plurality of said latchless surgical clips in said endoscopic section, each of Said latchless surgical clips having a pair of legs resiliently biased toward a closed position and movable away from each other to an open position;

b) distally advancing one of said latchless surgical clips to a pair of jaws positioned at a distal end of said endoscopic section by clip advancing means positioned within said endoscopic section;

c) positioning said latchless surgical clip adjacent body tissue to be clipped;

d) closing said jaws about said latchless surgical clip while permitting said clip legs to move toward the closed position, and substantially simultaneously repositioning said clip advancing means to a position proximal of the next clip to be advanced; and e) releasably locking said clip advancing means in said proximal position until released to advance the next clip.

* * * * *